US007944561B2

(12) United States Patent
Nisper et al.

(10) Patent No.: US 7,944,561 B2
(45) Date of Patent: *May 17, 2011

(54) MEASURING AN APPEARANCE PROPERTY OF A SURFACE USING A BIDIRECTIONAL REFLECTANCE DISTRIBUTION FUNCTION

(75) Inventors: Jon Kenneth Nisper, Grand Rapids, MI (US); Patrick S. Rood, Walker, MI (US); Brett Allen Pawlanta, Grand Rapids, MI (US); Thomas M. Richardson, Ada, MI (US); Brian Dale Teunis, Fennville, MI (US)

(73) Assignee: X-Rite, Inc., Grand Rapids, MI (US)

( * ) Notice: Subject to any disclaimer, the term of this patent is extended or adjusted under 35 U.S.C. 154(b) by 619 days.

This patent is subject to a terminal disclaimer.

(21) Appl. No.: 11/810,012

(22) Filed: Jun. 4, 2007

(65) Prior Publication Data

US 2007/0291993 A1    Dec. 20, 2007

Related U.S. Application Data

(63) Continuation-in-part of application No. 11/410,451, filed on Apr. 25, 2006.

(60) Provisional application No. 60/674,602, filed on Apr. 25, 2005.

(51) Int. Cl.
*G01N 21/55* (2006.01)
*G01J 3/46* (2006.01)

(52) U.S. Cl. ............ 356/445; 356/402; 356/448

(58) Field of Classification Search ................ None
See application file for complete search history.

(56) References Cited

U.S. PATENT DOCUMENTS

| 4,479,718 A | 10/1984 | Alman |
| 4,711,580 A | 12/1987 | Venable |
| 4,887,906 A | 12/1989 | Koehler |
| 5,137,364 A * | 8/1992 | McCarthy ............ 356/402 |

(Continued)

FOREIGN PATENT DOCUMENTS

DE        10143602 A1    4/2003

(Continued)

OTHER PUBLICATIONS

Baxter, et al., A *Viscous Paint Model for Interactive Applications*, University of North Carlolina at Chapel Hill, 2004, available at http://gamma.cs.unc.edu/VISCOUS/.

(Continued)

*Primary Examiner* — Tarifur Chowdhury
*Assistant Examiner* — Gordon J Stock, Jr.
(74) *Attorney, Agent, or Firm* — McCarter & English, LLP

(57) ABSTRACT

An apparatus for measuring a spatially under-sampled Bidirectional Reflectance Distribution Function (BRDF) of a surface. The apparatus may comprise a first light source directed to illuminate the surface from a first illumination direction, and a plurality of sensors positioned to receive light reflected by the surface. The plurality of sensors may comprise first, second and third sensors positioned to receive light reflected by the surface in first, second and third non-coplanar directions. In various embodiments, the apparatus may also comprise a computer in communication with the plurality of sensors. The computer is configured to convert light sensed by the plurality of sensors into a first appearance property of the surface considering the first, second, and third reflectance directions.

32 Claims, 18 Drawing Sheets

U.S. PATENT DOCUMENTS

| | | | |
|---|---|---|---|
| 5,231,472 | A | 7/1993 | Marcus et al. |
| 5,241,369 | A | 8/1993 | McNeil et al. |
| 5,313,542 | A | 5/1994 | Castonguay |
| 5,583,642 | A | 12/1996 | Nakazono |
| 5,640,246 | A | 6/1997 | Castonguay |
| 5,740,079 | A | 4/1998 | Shigemori et al. |
| 6,018,396 | A | 1/2000 | Rapaport et al. |
| 6,362,885 | B1 | 3/2002 | Osumi et al. |
| 6,373,573 | B1* | 4/2002 | Jung et al. ............. 356/419 |
| 6,539,325 | B1 | 3/2003 | Numata et al. |
| 6,557,397 | B2 | 5/2003 | Langsch |
| 6,577,397 | B1 | 6/2003 | Wadman |
| 6,707,553 | B1* | 3/2004 | Imura ............. 356/402 |
| 6,772,151 | B1 | 8/2004 | Johnston et al. |
| 7,064,830 | B2 | 6/2006 | Giorgianni et al. |
| 7,130,033 | B2 | 10/2006 | Delacour |
| 7,154,505 | B2 | 12/2006 | Coulthard |
| 7,259,852 | B2 | 8/2007 | Masuda |
| 7,277,174 | B2 | 10/2007 | Yamanouchi et al. |
| 7,466,415 | B2* | 12/2008 | Gibson et al. ............. 356/402 |
| 2001/0036309 | A1 | 11/2001 | Hirayama et al. |
| 2002/0060679 | A1* | 5/2002 | Malzbender et al. ......... 345/423 |
| 2002/0080136 | A1* | 6/2002 | Kouadio ............. 345/426 |
| 2002/0097400 | A1 | 7/2002 | Jung et al. |
| 2002/0163640 | A1 | 11/2002 | Masuda |
| 2002/0167669 | A1 | 11/2002 | Schwarz |
| 2004/0051874 | A1 | 3/2004 | Kubitzek |
| 2004/0218182 | A1 | 11/2004 | Alman et al. |
| 2004/0239919 | A1 | 12/2004 | Schwarz |
| 2005/0018195 | A1 | 1/2005 | Lex |
| 2006/0023202 | A1 | 2/2006 | Delacour |
| 2006/0245632 | A1 | 11/2006 | Nisper et al. |
| 2008/0291449 | A1 | 11/2008 | Rodrigues et al. |

FOREIGN PATENT DOCUMENTS

| | | |
|---|---|---|
| EP | 1217346 | 6/2002 |
| FR | 2860869 A1 | 10/2003 |
| WO | WO 2005/072448 A2 | 8/2005 |
| WO | WO 2008/063606 A2 | 5/2008 |
| WO | WO 2008/121358 A1 | 10/2008 |

OTHER PUBLICATIONS

Baxter, et al., *A Viscous Paint Model for Interactive Applications*, Computer Animation and Virtual Worlds Journal, Jul. 2004.

William V. Baxter, Jeremy Wendt, and Ming C. Lin, "IMPaSTo: A Realistic, Interactive Model for Paint." In Stephen N. Spencer (ed.), *Proceedings of the 3rd Internati onal Symposium on Non-Photorealistic Animation and Rendering*, Annecy, France, Jun. 5-7, 2004.

Caivano, Jose Luis, *Cesia: A system of Visual Signs Complementing Color*, Color research and application 16(4), Aug. 1991.

Caivano, Jose Luis, *The Representation of the Visual World in Photography*, Society for Imaging Science and Technology, 2008, p. 189-193.

Ershov, et al., *Reverse Engineering Approach to Appearance-Based Design of Metallic and Pearlescent Paints*, The Visual Computer, Oct. 12, 2004.

William Baxter and Ming Lin, *A Versatile Interactive 3D Brush Model*, Proc. of Pacific Graphics, Oct. 2004, available at http://gamma.cs.unc.edu/BRUSH/.

William V. Baxter, Vincent Scheib, Ming C. Lin, and Dinesh Manocha "DAB: Interactive Haptic Painting with 3D Virtual Brushes." In Eugene Fiume (ed.), *Proceedings of the 28th Annual Conference on Computer Graphics and Interactive Techniques, SIGGRAPH 2001*, Los Angeles, CA, Aug. 12-17, 2001, pp. 461-468. Available at http://gamma.cs.unc.edu/DAB/.

Curtis, et al., "Computer Generated Watercolor." In *SIGGRAPH 2001*, Los Angeles, CA, Aug. 3-8, 1997, pp. 461-468. Available at http://grail.cs.washington.edu/projects/watercolor/.

Nelson S.-H. Chu and C.-L. Tai, Real-time Painting With an Expressive Virtual Chinese Brush. *IEEE Computer Graphics and Applications*, Sep./Oct. 2004 (vol. 24, No. 5). pp. 76-85.

Nelson S.-H. Chu and C.-L. Tai, An Efficient Brush Model for Physically-Based 3D Painting, *Proc. of Pacific Graphics 2002*, Oct. 9-11, Beijing, China, IEEE Press.

Jeng-Sheng Yeh, Ting-Yu Lien, Ming Ouhyoung, "On the Effects of Haptic Display in Brush and Ink Simulation for Chinese Painting and Calligraphy", Proc. of Pacific Graphics 2002 (PG2002), pp. 439-441, Oct. 2002, Beijing, China, IEEE Press.

http://www.refractometer.com/abberefrac.html (as of Mar. 16, 2006 using wayback machine).

http://www.microphotonics.com/se500.html (as of Mar. 13, 2006 using wayback machine).

http://www.datacolor.com/uploads/broch_multifx10_en.pdf (as of Mar. 13, 2006 using wayback machine).

BBC News, *Laser spots paper 'fingerprints'*, available at http://news.bbc.co.uk/2/hi/technology/4741809.stm, Aug. 3, 2005.

X-Rite, The Color Guide and Glossary, Communication, Measurement, and Control for Digital Imaging and Graphic Arts, 2004.

Ershov, et al., Rendering Pearlescent Appearance Based on Paint-Composition Modelling, Eurographics, 2001, vol. 20 No. 3.

Harvey, Light Scattering Properties of Optical Surfaces, Dissertation, University of Arizona, 1976.

Standard Practice for Goniometric Optical Scatter Measurements, ASTM International; Designation: E 2387-05, Feb. 2005.

* cited by examiner

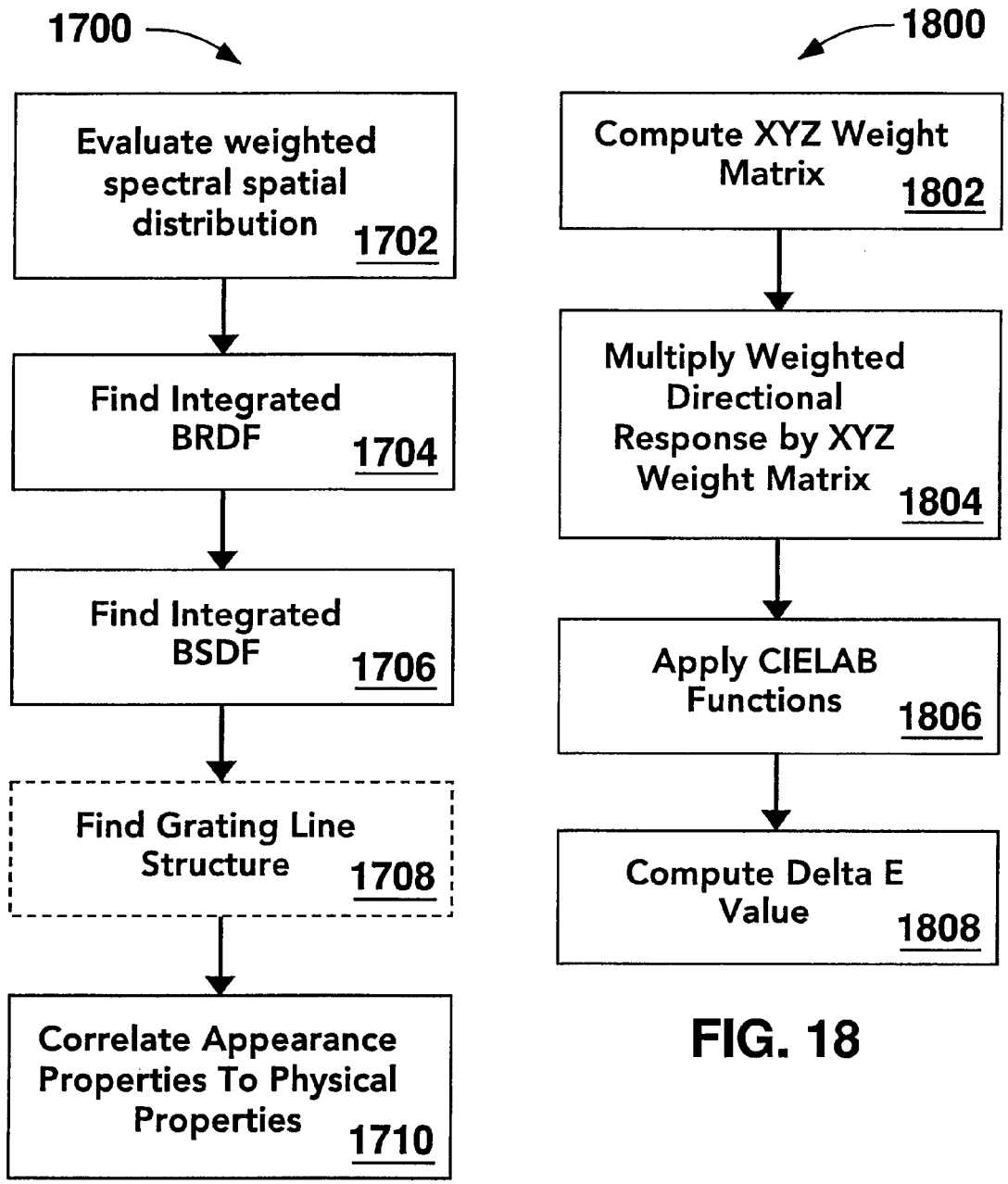

MEASURING AN APPEARANCE PROPERTY OF A SURFACE USING A BIDIRECTIONAL REFLECTANCE DISTRIBUTION FUNCTION

CROSS-REFERENCE TO RELATED APPLICATION

This application is a continuation-in-part and claims the benefit of a co-pending non-provisional patent application entitled "Measuring an Appearance Property of a Surface Using a Spatially Undersampled Bidirectional Reflectance Distribution Function," which was filed on Apr. 25, 2006 and assigned Ser. No. 11/410,451, which in turn claimed priority to U.S. Provisional Application No. 60/674,602, filed on Apr. 25, 2005. Both of the foregoing applications are incorporated herein by reference.

BACKGROUND

Many methods and devices have been developed for measuring and describing the visual appearance of objects. These methods and devices are useful in a variety of contexts. For example, measurements of the visual appearance of an object can reveal properties of any paints, pigments, specialty coatings, surface treatments, etc., that may be present on the object. Also, for example, measurements of the visual appearance of an object can be used to create computer models, set production tolerances, etc. It is known to use various devices to provide spectral measurements of a surface of an object. Existing devices, however, either produce results of limited detail or are exorbitant in cost, size, and the time necessary for measurements.

For example, it is known to use discrete multi-angle spectrometers that measure reflectance over a limited number of viewing and illumination directions. An example of such a device is the MA68 available from X-RITE. All of these devices, however, either consider a limited number of viewing directions (e.g., coplanar directions), or consider data derived from all viewing angles together, for example, by summing or averaging over all directions. As a result, advantageously used to generate a weighted vector sum based on values for the various measurement directions, with the weights being determined and implemented based on reflectance factors for each direction. The result of this sum is a spectrum of points in 2D or 3D space, one point for each measured wavelength, which represent "fingerprint" values for the surface-of-interest. The weighted vector sum is also generally scaled by the length of the vector sum of an ideal white Lambertian reflector for enhance comparability of the fingerprint values for the surface-of-interest relative to typical reflectance values. In an exemplary implementation, the coordinate system for DNA consists of the specular direction (z axis), the projection of the illumination direction orthogonal to the specular direction (y axis), and the cross product of these two directions (x axis).

For purposes of the present disclosure, a measurement direction is described with reference to the angle it makes with the specular direction and by its angle of rotation about the specular axis from the positive y axis. A measurement with an illumination direction that makes an angle of $\Lambda'$ with surface normal, and a measurement direction that makes an angle of $\Phi°$ with specular, and has angle of rotation $\Theta°$ about specular, is described as $\Lambda as\Phi az\Theta$. The (x,y,z) coordinates of the measurement direction $\Lambda as\Phi az\Theta$ are then $(\sin(\Phi)*\sin(\Theta)), \sin(\Phi)*\cos(\Theta), \cos(\Phi))$.

To further illustrate DNA processing and the applicability thereof for purposes of the present disclosure, an exemplary implementation thereof is described. Thus, for a measurement consisting of 10 directions, and 31 wavelengths with 10 nm spacing from 400 nm to 700 nm, exemplary measurement directions are 45 as-15az0, 45as15az0, 45as25az-90, 45as25az0, 45as25az90, 45as45az0, 45as60az-54.7, 45as60az54.7, 45as75az0, and, 45 as110az0. The (x,y,z) coordinates and reflectance factors for these directions are (0, −0.26, 0.97), (0, 0.26, 0.97), known discrete multi-angle spectrometers provide results that do not reflect directional variations in surface appearance. Referring to the coatings industry, these results can be useful to measure some properties of surfaces including conventional paints, pigments, and coatings. They are not as useful, however, for measuring properties of surfaces having specialized paints, pigments, and other specialty coatings that have different appearances when viewed from different angles, such as those that appear today on cars, boats, currency, consumer plastics, cosmetics, etc. For example, limited sample multi-angle spectrometers are not as useful for measuring properties of interference coatings such as, for example, pearlescent automotive paints that appear one color (e.g., white) from one angle and a second color (e.g., pink) from another angle. They also typically do not provide detailed enough results to tie properties of a surface back to physical features of the surface, for example, due to coating formulation and/or application process factors.

Some of the shortcomings of known discrete multi-angle spectrometers are addressed by devices that measure the complete Bidirectional Reflectance Distribution Function (BRDF) of a surface, such as goniospectrophotometers and parousiameters. The complete BRDF generated by these devices provides a rich characterization of the scatter off of a surface as a function of illumination angle, viewing angle, wavelength and other variables. Both of the known devices for measuring BRDF, however, have significant drawbacks.

Goniospectrophotometers, such as the GCMS-4 Gonio-Spectro-Photometric Colorimeter available from MURAKAMI, measure the complete BRDF by scanning both illumination and detection angles, typically over a complete hemisphere. Although they can provide good results, the devices are extremely large and expensive. Also, it can take several hours to scan illumination and detection angles over a complete hemisphere, making real-time applications impossible. Parousiameters, such as the one described in U.S. Pat. No. 6,557,397 to Wademan, measure the complete BRDF by projecting a range of illumination and detection angles onto a hemispheric screen and imaging the screen using a camera. The error of these devices, however, is directly related to the size of the hemispherical screen, and the devices cannot acceptably measure samples with an area greater than 10% of their screen's area. As a result, parousiameters are often large and bulky. Also, slots in the screen, and the limited dynamic range of most high resolution cameras further limit the device. In addition, because both goniospectrophotometers and parouiameters measure illumination and viewing angles over a complete hemisphere, noise issues can become a significant factor.

SUMMARY

In one general aspect, the invention is directed to an apparatus for measuring a spatially under-sampled Bidirectional Reflectance Distribution Function (BRDF) of a surface. The apparatus may comprise a first light source directed to illuminate the surface from a first illumination direction, and a plurality of sensors positioned to receive light reflected by the surface. The plurality of sensors may comprise first, second and third sensors positioned to receive light reflected by the surface in first, second and third non-coplanar directions. In various embodiments, the apparatus may also comprise a computer in communication with the plurality of sensors. The computer is configured to convert light sensed by the plurality of sensors into a first appearance property of the surface considering the first, second, and third reflectance directions.

In another general aspect, the invention is directed to methods for measuring a spatially under-sampled Bidirectional Reflectance Distribution Function (BRDF) of a surface. The methods comprise the steps of illuminating the surface with a first light source incident on the surface from a first illumination direction, and sensing light of a plurality of wavelengths reflected by the surface in a plurality of reflectance directions. The plurality of reflectance directions include a first reflectance direction, a second reflectance direction and a third reflectance direction. The methods also comprise the step of converting the light into a first appearance property of the surface considering the first, second, and third reflectance directions.

Various other embodiments of the invention are directed to systems for measuring a spatially under-sampled Bidirectional Reflectance Distribution Function (BRDF) as well as practical applications. In various aspects, the invention is directed to methods of matching the appearance of coatings applied to two components, methods of repairing a device, and methods of finding the identity of an unknown object.

BRIEF DESCRIPTION OF THE FIGURES

Embodiments of the present invention are described herein, by way of example, in conjunction with the following figures, wherein:

FIGS. 17-22 show flow charts illustrating process flows according to various embodiments of the present invention;

DETAILED DESCRIPTION OF THE INVENTION

Embodiments of the present invention are directed to methods and apparatuses for measuring and/or analyzing a spatially under-sampled Bidirectional Reflectance Distribution Function (BRDF) of a surface. When light is incident on a surface, a portion of the light is reflected, scattered or otherwise directed away from the surface over various directions. The BRDF of a surface is an expression of the intensity of this reflectance over all or multiple wavelengths and reflectance directions as a function of illumination angle and other variables (e.g., polarization). According to various embodiments, the BRDF of a surface is spatially under-sampled by measuring the intensity of reflectance at only a discrete number of reflectance directions. In various embodiments, the discrete reflectance directions may be non-coplanar. The measured reflectance may then be processed to derive one or more appearance properties of the surface under observation. The appearance properties may reflect directional variation in the appearance of the surface, as captured by the measured reflectance.

Figure 1:
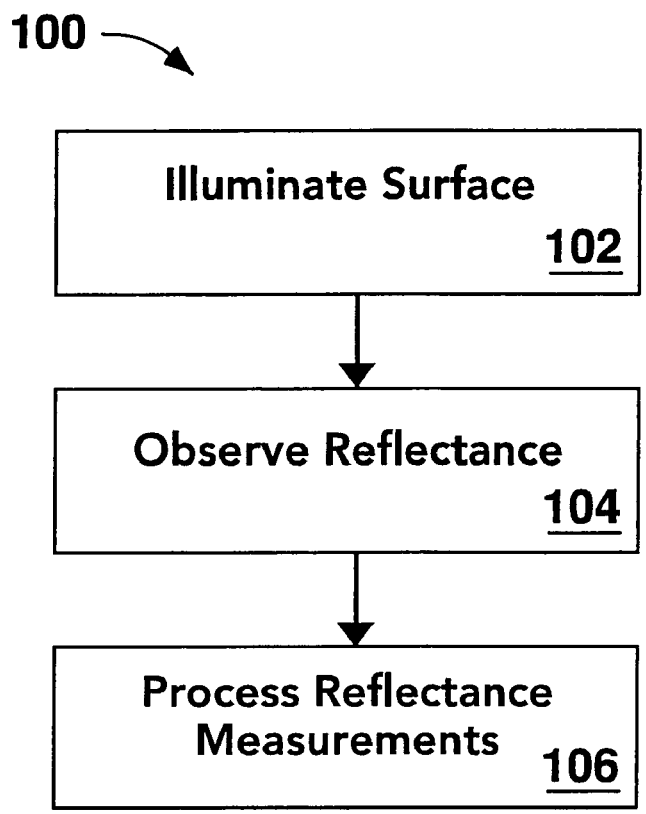
FIG. 1 shows a flow chart illustrating a process flow according to various embodiments of the present invention.

FIG. 1 shows a flow chart illustrating a process flow 100 for measuring and processing a spatially under-sampled BRDF of a surface according to various embodiments. At step 102, light may be directed toward the surface. The light may be formed into one or more beams, which may be collimated or non-collimated. The light may originate from one or more broad spectrum illumination sources and may be incident on the surface from one or more illumination directions. The number of illumination sources and illumination directions may vary based on the particular application. It will be appreciated, however, that increasing the number of illumination sources and/or directions may increase the quality of the resulting BRDF. It will be appreciated that, the illumination direction or directions may form any angle with the surface normal. In various embodiments, however, the illumination direction or directions may form angles with the surface normal of between zero and sixty-five degrees (e.g., zero degrees, 45 degrees, etc.).

At step 104, the intensity of the reflectance off of the surface in a plurality of discrete reflectance directions may be measured. It will be appreciated that these measured reflectances, along with the corresponding reflectance directions, represent a spatially under-sampled BRDF of the surface. In various embodiments, the complete set of reflectance directions may be non-coplanar. Also, in various embodiments, multiple measurements may be taken at each reflectance direction, with each measurement recording the reflectance intensity at a particular wavelength or wavelength range. In various embodiments, the measurements may be taken from fixed sensors, with one sensor fixed on each of the plurality discrete reflectance directions. It will be appreciated that because the reflectance is being measured only in discrete directions, and not in every direction, that the time necessary to measure the reflectance may be less than that taken by complete BRDF devices (e.g., goniospectrophotometers and parousiameters). In various embodiments, the measurements may be taken in under five seconds.

The spatially under-sampled BRDF may be expressed as a series of reflectance vectors representing the observed intensities at each reflectance direction. For example, each observed reflectance direction may have a vector pointing in the reflectance direction with a magnitude equal to the observed reflectance intensity in the reflectance direction. It will be appreciated that if multiple wavelengths or wavelength ranges are observed in a reflectance direction, then reflectance directions may have a vector corresponding to each of the wavelengths or wavelength ranges.

Figure 2:
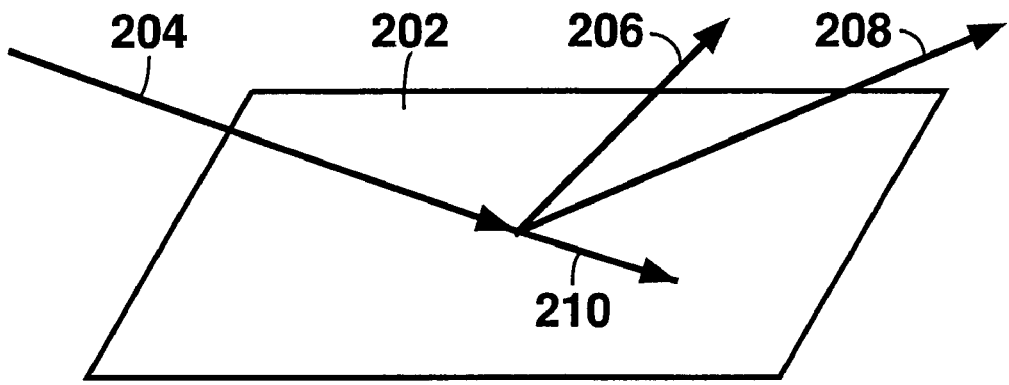
FIG. 2 shows a diagram of reflectance from a surface according to various embodiments of the present invention.
Figure 3:
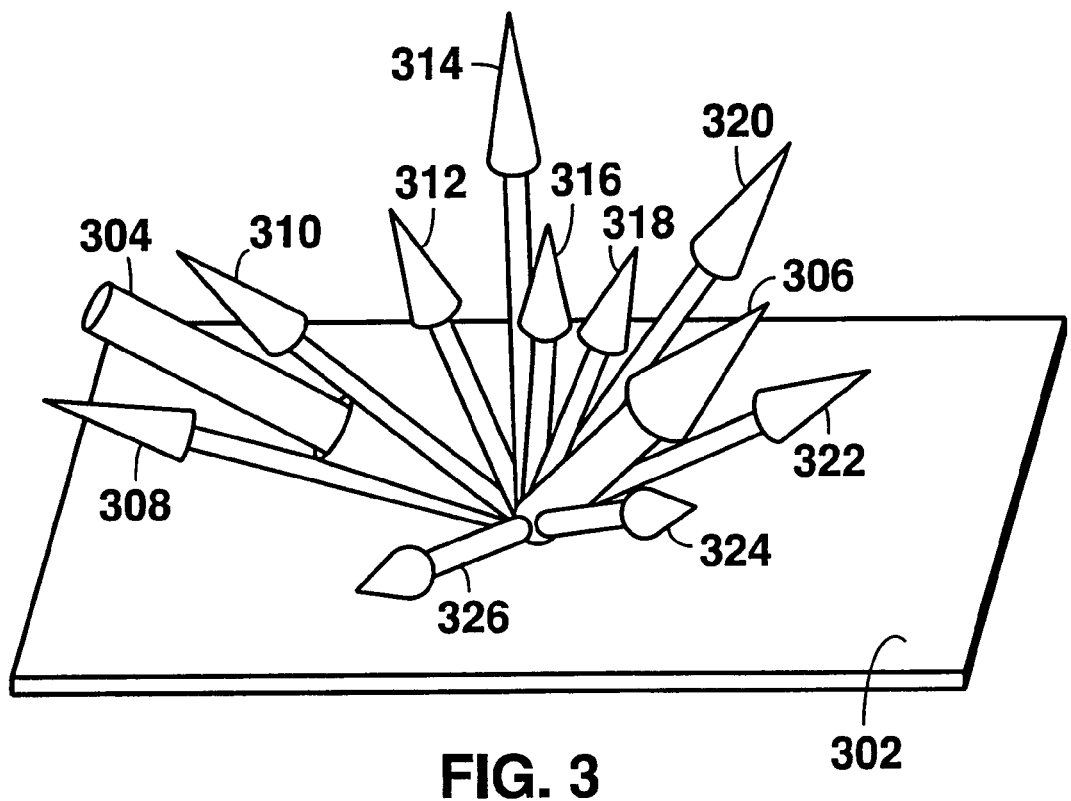
FIG. 3 shows a diagram of reflectance from a surface according to various embodiments of the present invention.

As an illustration, FIG. 2 shows an exemplary surface 202 with light incident on the surface 202 from an illumination direction 204. Three discrete non-coplanar reflectance directions 206, 208, 210 are observed. FIG. 3 shows another exemplary surface 302 according to various embodiments having incident light from one illumination direction 304 and eleven observed reflectance directions 306, 308, 310, 312, 314, 316, 318, 320, 322, 324 and 326. It will be appreciated that the number and identity of the reflectance directions may vary. For example, in various embodiments, there may be between five and fifteen reflectance directions. Also, in various embodiments, the reflectance directions may include industry standard reflectance directions (e.g., those having aspecular angles of 15, 25, 45, 75 and 100 degrees.) Also, in various embodiments, at least one of the reflectance directions may be chosen orthogonal to the illumination direction relative to a surface normal of the surface.

Figure 4:
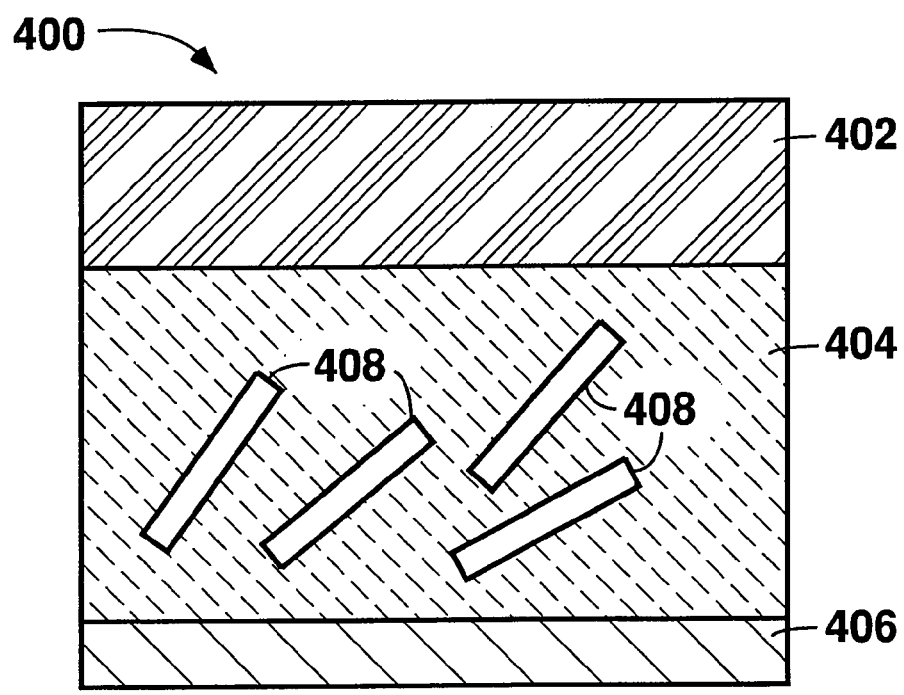
FIG. 4 shows a diagram of a surface coating according to various embodiments of the present invention.

In various embodiments, the number of observed reflectance directions may be chosen based on a desired resolution of results and/or the complexity of the surface to be measured. For example, each layer and/or materials contained in the layers of a surface may have a number of physical properties (e.g., roughness, local slope, curvature, real and imaginary portions of the index of refraction, etc.). In various embodiments, it may only be necessary to measure a minimum number of reflectance directions to obtain enough independent relationships to solve for all desired variables. For example, a minimum number of observed reflectance directions may be chosen according to the following:

$$\text{Minimum Number of Reflectance Directions} = 2L + M \qquad (1)$$

where L is the number of physical layers of the surface through which light can potentially scatter, and M is the number of different materials contained in the layers (e.g., pigments, metallic flakes, etc.). For example, FIG. 4 shows an exemplary surface 400 that may be observed according to various embodiments. The surface 400 has a specialty coating, such as, for example, an interference or pearlescent coating, discussed above. The surface 400 includes three layers, clear coat 402, pigment layer 404 and substrate 406, as well as one material contained in the layers (e.g., metal flakes 408). Accordingly, a minimum number of observed reflectance directions for the surface 400 would be seven. It will be appreciated that useful readings may be obtained using less than the minimum number of reflectance directions according to Equation 1, however, in that case, the observed reflectance may not capture the contribution to BRDF from each of the surface features.

As the number of observed discrete reflectance directions is increased, the quality of the results obtained may also increase. For example, in various embodiments, additional physical properties may be measured. It will be appreciated however, that increasing the number of observed discrete reflectance directions will also increase the complexity, time necessary to observe at all reflectance directions, and noise. Accordingly, in various embodiments, it may not be necessary to observe more reflectance directions than the following:

$$\text{Maximum Number of Reflectance Directions} = 6L + 6M \qquad (2)$$

where L and M are defined as above. Equation 2 may define the number of reflectance directions necessary to have an independent relationship for each physical property to be measured.

Figure 5:
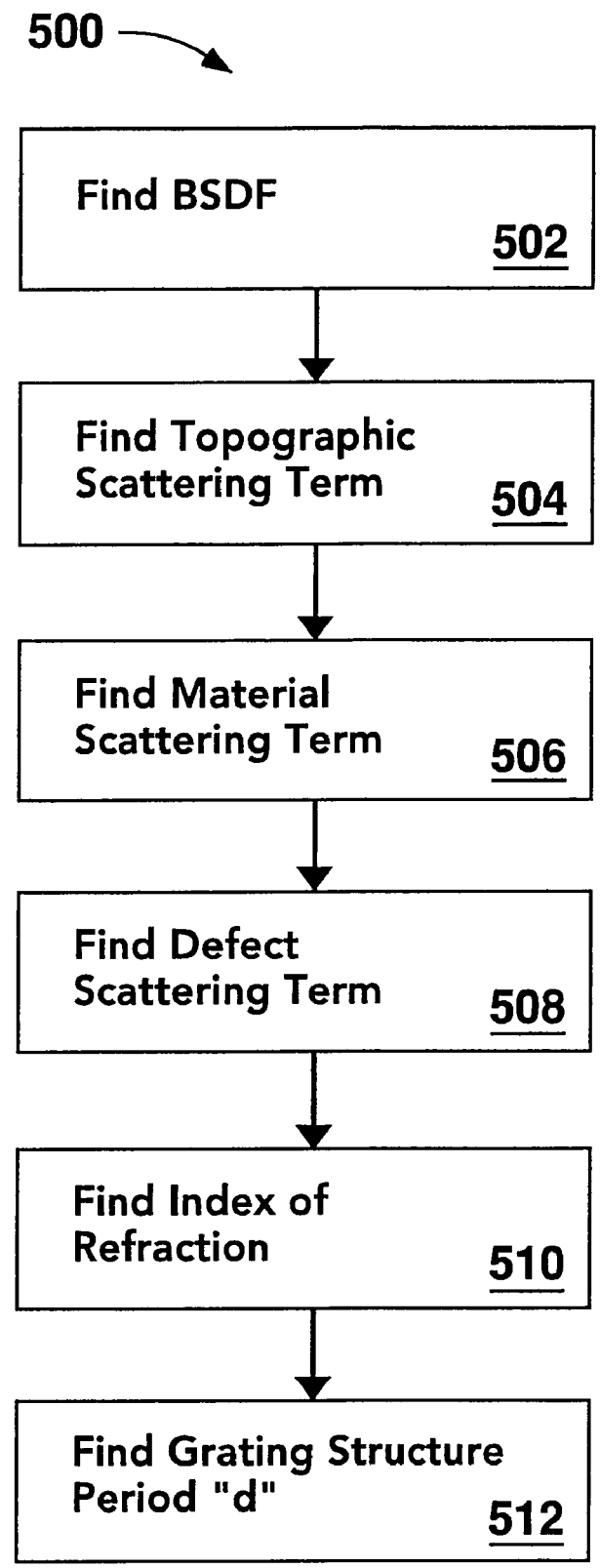
FIG. 5 shows a flow chart illustrating a process flow according to various embodiments of the present invention.
Figure 8:
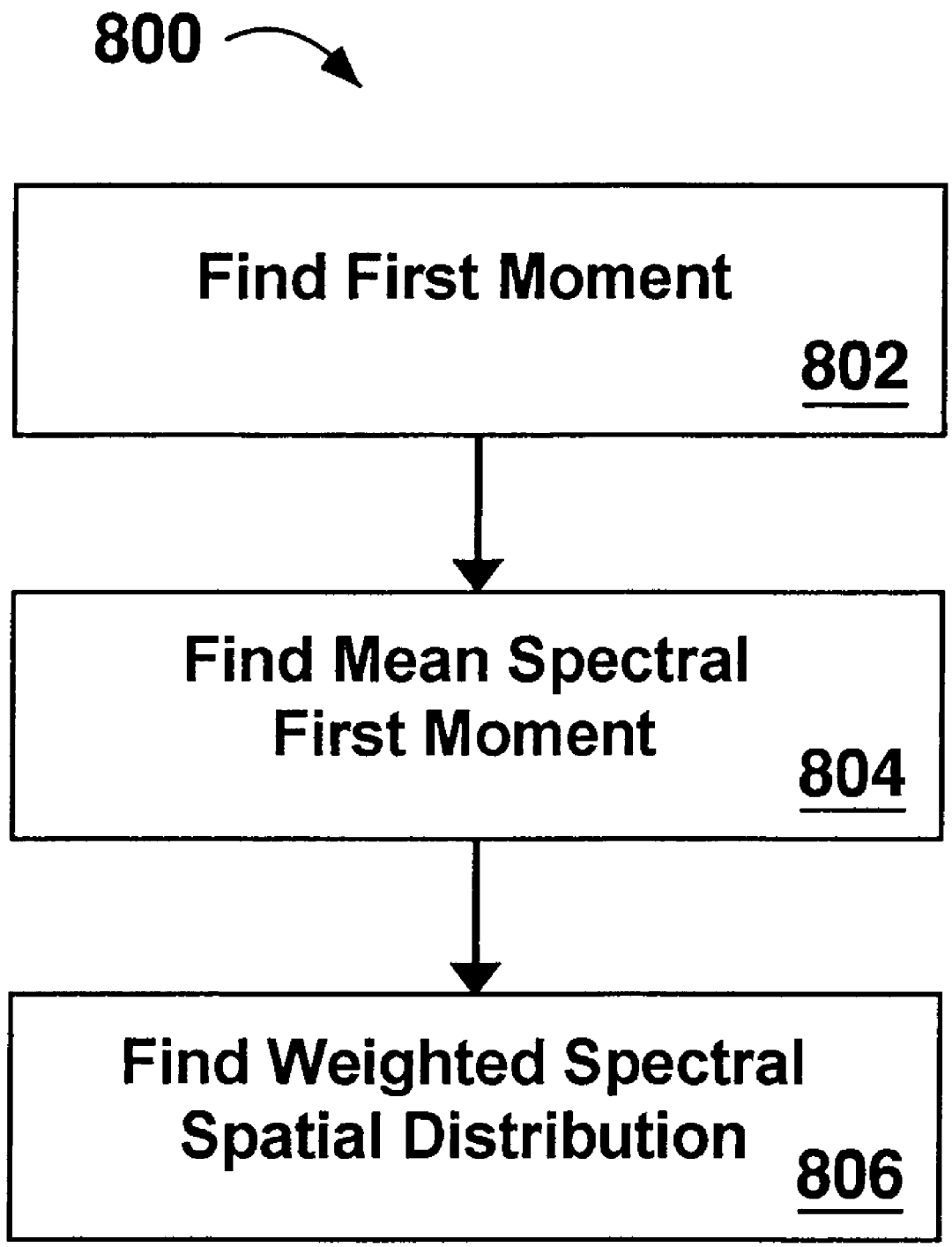
FIG. 8 shows a flow chart illustrating a process flow according to various embodiments of the present invention.

Referring back to FIG. 1, at step 106, the reflectance measured at step 104 may be processed to generate an appearance property or properties of the surface. The spatially undersampled BRDF itself may be considered an appearance property of the surface, though it will be appreciated that other appearance properties may be generated, for example, by manipulating the BRDF. At least one of the appearance properties may reflect directional differences in the appearance of the surface that are inherent in the measured reflectance intensities and directions. In various embodiments, additional appearance properties may be found by performing manipulations to the BRDF. For example, FIG. 5 shows a process flow 500, described below, for processing measured reflectance by plugging the measured reflectance into a mathematical model for the BRDF of the surface and performing certain mathematical manipulations. As another example, FIG. 8 shows a process flow 800 for analyzing various moments of the BRDF data.

The appearance properties generated at step 106 may yield information about the composition and features of the surface under measurement (e.g., physical properties). For example, in the coatings industry, properties of the formulation and application process of any coatings present on the surface may be found. For some physical properties, closed form solutions may exist that allow values for the properties to be derived directly from the measured reflectance or BRDF. For example, as discussed below, a grating structure period may be derived from the BRDF, and may relate directly to the distance between regularly spaced features of the surface. Also, some physical properties may be derived using experimental methods. For example, appearance properties of surfaces with known physical properties may be measured. A database may then be created showing correlations between appearance properties and physical properties. When a surface with unknown physical properties is measured, appearance properties (e.g., BRDF, and/or values derived therefrom) may be compared to the database to find the unknown physical properties.

FIG. 5 shows the process flow 500 for processing measured reflectance (e.g., BRDF) and deriving additional appearance properties of the surface using mathematical models based on the BRDF. Referring to FIG. 5, at step 502, the BRDF may be converted to a Bidirectional Scatter Distribution Function (BSDF). The BSDF represents the portion of the BRDF due to scattering of incident light. To calculate the BSDF, the specular component of BRDF is subtracted from the BRDF. The specular component is that portion of the BRDF that is due to Fresnel reflection of incident light. The specular component is concentrated in a reflectance direction that is related to the illumination direction such that the angle of incidence of the illumination direction is equal to the angle of reflectance of the specular reflectance direction. For example, referring to FIG. 3, the illumination direction 304 forty-five degrees from the surface and 45 degrees from the surface normal. Accordingly, the specular component is directed in reflectance direction 306, which is also 45 degrees from the surface and surface normal. It will be appreciated that if there is more than one illumination direction, then the specular component may be concentrated in more than one angle.

The specular component may be subtracted from the BRDF in a number of different ways. For example, one of the observed reflectance directions may be the specular direction. In this case, the BSDF may be found by subtracting the contribution of this reflectance direction from the overall BRDF. In embodiments where the specular direction is not one of the observed reflectance directions, then the specular component may be approximated based on the responses at observed reflectance directions near the specular direction. The approximation of the specular component may then be subtracted from the BRDF.

Referring again to FIG. 5, a topographic scattering term of the BSDF may be found at step 504. It will be appreciated that the BSDF may be expressed as:

$$BSDF=(16\pi^2/\lambda^4)\cos^2\theta_i\Phi_{ba}(\phi_s)R_a(\theta_i)S_z(f) \quad (3)$$

where $S_z(f)$ is the two dimensional Power Spectral Distribution (PSD) of any height fluctuations (Z) of the surface. Accordingly, dividing the BSDF by $(16\pi^2/\lambda^4)\cos^2\theta_i$ yields a topographic scattering term that is proportional to height fluctuations on the surface.

At step 506, a material scattering term may be found. The material scattering term may be indicative of fluctuations in the composition or density of the surface material (e.g., homogeneity, bubbles, inclusions, randomly dispersed or distributed pigments smaller than approximately 30 microns, etc.). It will be appreciated that the BSDF may be expressed as:

$$BSDF=(1/\lambda^2)\Phi_{ba}(\phi_S)R_a(\theta_i)S_m(f) \quad (4)$$

where $S_m(f)$ is the PSD of the perturbation of the material response for scattering. This PSD may be related to specific models of the material inhomogeneities, such as the magnitudes and spatial distribution of variations in composition. A material scattering term may then be found by dividing the BSDF by $(1/\lambda^2)$. Experimental methods may be used to tie values of the material scattering term (e.g., an appearance property) to particular types, sizes, etc. of fluctuations in composition and/or density of the surface (e.g., physical properties).

At step 508, a defect scattering term of the BSDF may be found. Defect scattering occurs when a surface feature or bulk property perturbation is localized and/or isolated spatially (e.g., pits or bumps in the surface, individual inclusions in an otherwise homogeneous bulk material). It will be appreciated that, if the defects are randomly distributed, then the BSDF may be expressed as:

$$BSDF=(1/\lambda^2)\Phi_{ba}(\phi_S)R_a(\theta_i)S_d(f) \quad (5)$$

where $S_d(f)$ is the PSD of the collection of defects in the surface. Accordingly, a defect scattering term may be calculated by dividing the BSDF by $(1/\lambda^2)$. Experimental methods may be used to tie particular values of the defect scattering term to particular defect types and locations. It will be appreciated from comparing Equations 4 and 5, that $S_d(f)$ and $S_m(f)$ may have the same value. Accordingly, Equation 4 may be applied to a surface that is measured or assumed to be relatively free of blemishes. On the other hand, Equation 5 may be applied to surfaces with known defects.

Figure 6:
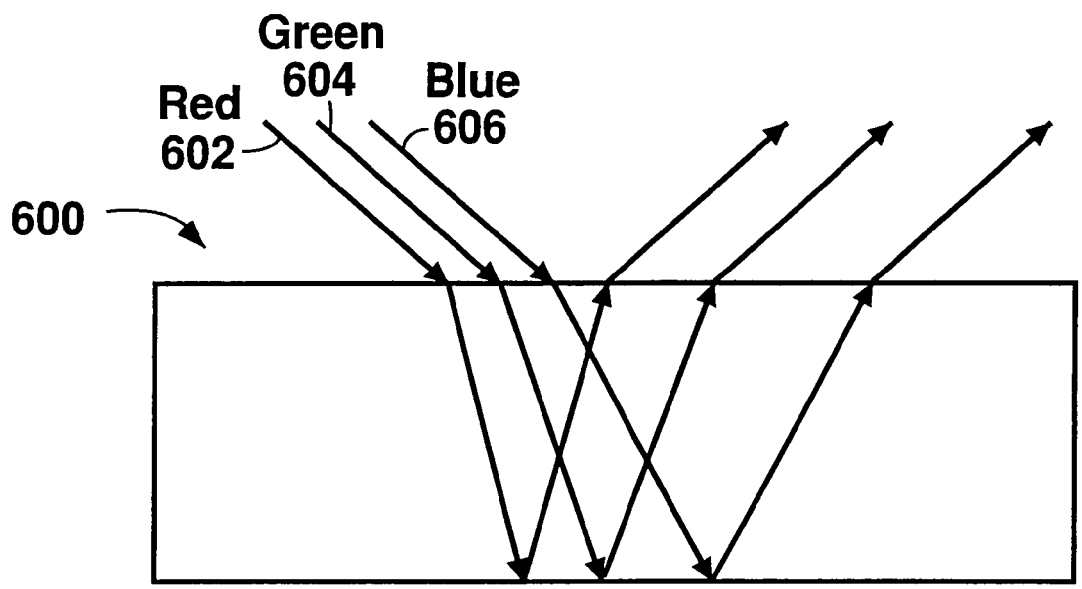
FIG. 6 shows a diagram of refraction by a surface according to various embodiments of the present invention.

At step 510, an index of refraction of the surface may be found. FIG. 6 shows a surface 600 having red 602, green 604, and blue 606 beams incident thereon. FIG. 6 illustrates how refraction may cause the different beams 602, 604, 606 to behave differently. Snell's law may be used to find the index of refraction of the surface as follows:

$$n_1 \sin\theta_1 = n_2 \sin\theta_2 \quad (6)$$

where $n_1$ is the index of refraction of the surface, $n_2$ is the index of refraction of the medium between the surface and the observation points, $\theta_1$ is the angle of the illumination direction and $\theta_2$ is the refraction angle at a given wavelength. The index of refraction may be considered a physical property of the surface, however, it will be appreciated that additional physical properties (e.g., the grating structure period below) may be derived based on the index of refraction.

Figure 7:
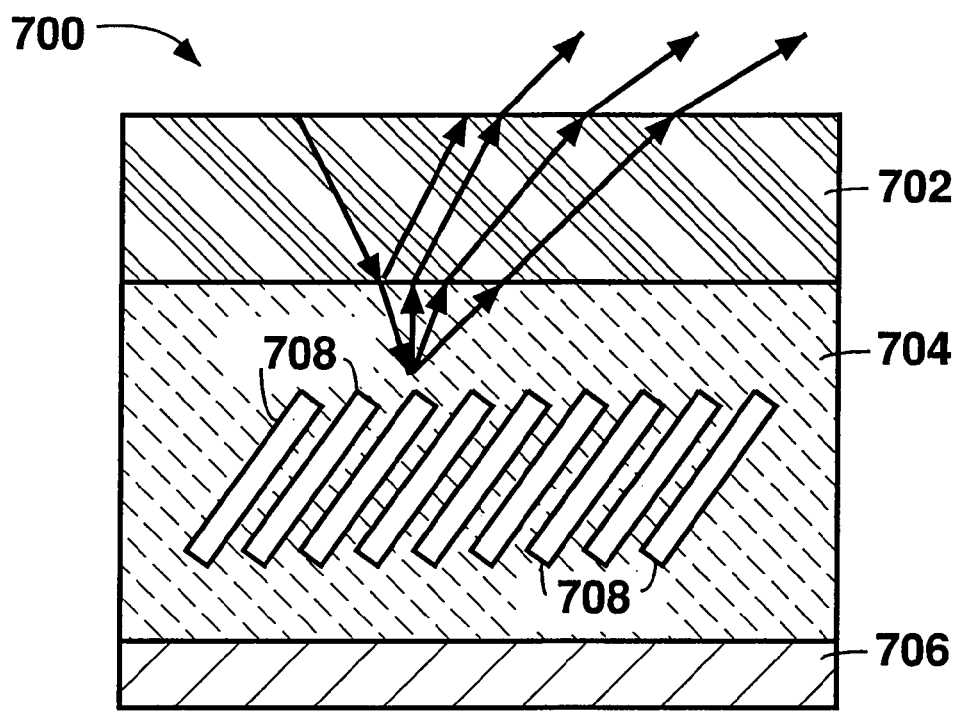
FIG. 7 shows a diagram of diffraction and/or interference by a surface according to various embodiments of the present invention.

At step 512, a grating structure period of the surface may be found. The grating structure period may provide information about surface features, interface features, bulk material structure, pigments, particles, flakes, etc., present in the surface that have an ordered structure. Such ordered features may cause diffraction and/or interference in reflected light based on the grating structure period of the features. For example, FIG. 7 shows an exemplary surface 700 having a series of flakes 708 embedded therein at a regular or semi-regular interval and orientation. Note that the surface 700 may include a plurality of layers 702, 704 and 706. The grating structure period of the surface 700 may reflect the distance between and/or orientation of the flakes 708. The grating structure period may be found as follows:

$$\lambda = 2nd \sin(\theta) \quad (7)$$

where n refractive index of the surface, d is the period of the grating line structure and θ is the angle at which the wavelength of light is diffracted normal to the grating line structure.

FIG. 8 shows a process flow 800 for deriving values indicative of surface properties using a moment or moments of the BRDF. At step 802 a first moment, or weighted directional response may be found. The weighted direction response may be the vector summation of all of each of the vectors representing the observed intensities and reflectance directions over a given wavelength or wavelength range. It will be appreciated that where multiple wavelengths or wavelength ranges are considered, a weighted directional response may be calculated for each of the considered wavelengths or wavelength responses.

In various embodiments weighting factors may be applied to one or more of the observe reflectance directions. For example, the weighting factors may be chosen so that the resulting weighted BRDF more closely approximates a geometrically uniform distribution of reflectance directions. In various embodiments, weighting factors may be chosen to accentuate reflectance directions that have increased significance for certain surface types. For example, when the surface includes an interference pigment, the reflectance direction having an aspecular angle of −150 may be disproportionately weighed, when the surface includes a retroreflective material, reflectance directions having aspecular angles of 75° and 110° may be disproportionately weighted.

Also, in various embodiments, weighting factors may be chosen to be compatible with various standards. For example, the DIN 6175-2 standard defines color difference formulas with weighting functions that depend on the standard measurement angles, (e.g., the 15/25/45/75/110 angles described above). In various embodiments, the weighting factors may be chosen based on human perceptual studies (e.g., the reflectance directions that humans most strongly perceive may be given higher weighting factors).

It will be appreciated that the weighting factors may also be chosen to more accurately represent the distribution of energy reflected off the surface. For example, if the total energy reflected off the surface is 20 mW, and it is expected that a disproportionately high portion of the 20 mW is expected to be reflected in a certain range of reflectance directions, then intensity measurements taken in that range of reflectance directions may be given a relatively higher weighting compared to other directions. In this way, the spatially undersampled BRDF may more closely match the actual energy distribution modeled by the full BRDF.

The weighted directional response may be tied to various properties of the surface. For example, in the case of a surface having a coating, the weighted directional response may be used to identify application process variations between two surfaces. For example, when two surfaces differ only in the application process of a coating on the surfaces, the weighted directional response of the first surface can typically be transformed into the weighted directional response of the second surface. The necessary translations, rotations and scaling can be experimentally tied to particular application process variations.

At step 804, a mean spectral first moment of the surface may be found. The mean spectral first moment may be a vector whose direction represents the average spectral first moment. A weighted spectral spatial distribution function may be found at step 806. The weighted spectral spatial distribution may be a function that describes the general line shape defined by the directional endpoints of the weighted directional response. Both of these appearance properties (e.g., the mean spectral first moment and weighted spectral spatial distribution) may be experimentally tied to various physical properties of the surface.

Figure 9:
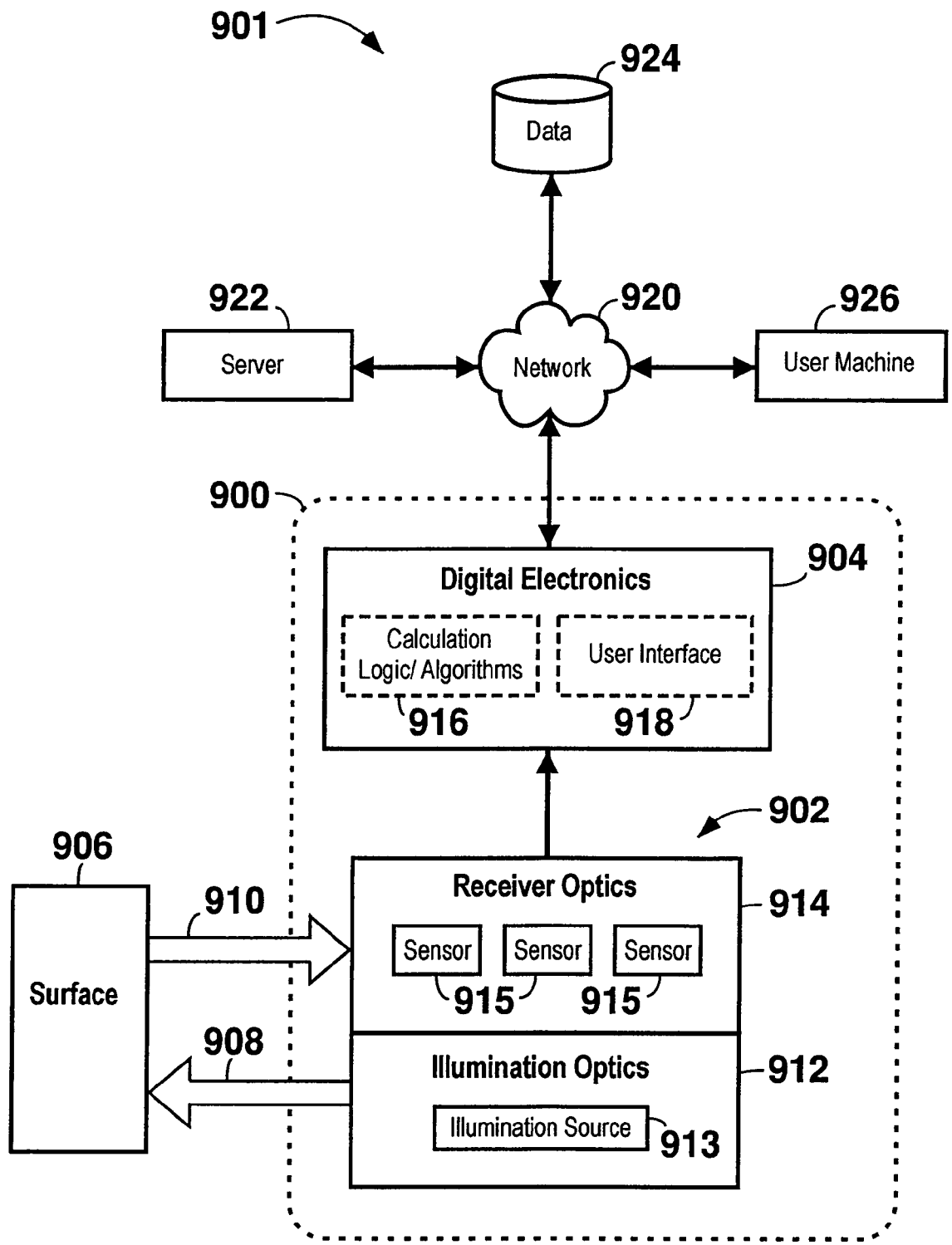
FIG. 9 shows a diagram of a system according to various embodiments of the present invention.

FIG. 9 shows a diagram of a system 901 that may be used to implement methods of measuring and/or analyzing a spatially under-sampled BRDF of a surface, for example, as described above, according to various embodiments. The system 901 includes a measuring device 900, and may also include various other information storage, processing and/or interface devices such as, for example, a server 922, a user machine 926 and/or a database 924. The various devices 900, 922, 924, 926 of the system 901 may be in contact with one another via a network 920, which may be any suitable type of wired or wireless network.

In various embodiments, the measuring device 900 may include an optics unit 902 and an electronics unit 904. The optics unit 902 may include illumination optics 912 configured to direct light 908 towards a surface 906 under inspection, and receiver optics 914 for receiving and sensing the reflectance 910 of the light 908 off of the surface 906. For example, the illumination optics 912 and receiver optics 914 may sense a spatially under-sampled BRDF of the surface 906 as described above. The electronics unit 904 may process the reflectance results generated by the optics unit 902. In various embodiments, the electronics unit 904 may include calculation logic 916 for deriving appearance properties of the surface and/or relating appearance properties to physical properties. A user interface module 918 may present results (e.g., raw reflectance data, appearance properties, physical properties, etc.) to a user of the device 900. In various embodiments, some or all of the processing and presenting of results may be performed by other components of the system for processing (e.g., server 922, database 924, user machine 926). For example, the server 922 and/or user machine 926 may perform processing to derive appearance and/or physical properties; results of the processing may be presented to a user through the user machine 926; and the database 924 may store experimental correlations between measured reflectance and surface properties.

Referring back to the optics unit 902, the illumination optics 912 may include one or more illumination sources 913 configured for directing light 908 toward the surface 906 from one or more illumination directions. The illumination sources 913 may include any kind of suitable illumination source including, for example, an incandescent source, a white LED, etc. In various embodiments, each illumination source 913 may include a plurality (e.g., nine) LED's of various spectral outputs. The LED's may be positioned on a leadless chip carrier or any other kind of installation technology. It will be appreciated that the illumination source or sources 913 may generate light across the wavelengths that are to be measured by the receiver optics 914 as described herein below. In various embodiments, the illumination sources 913 may be configured to generate collimated or non-collimated beams, for example, as described above.

Figure 16:
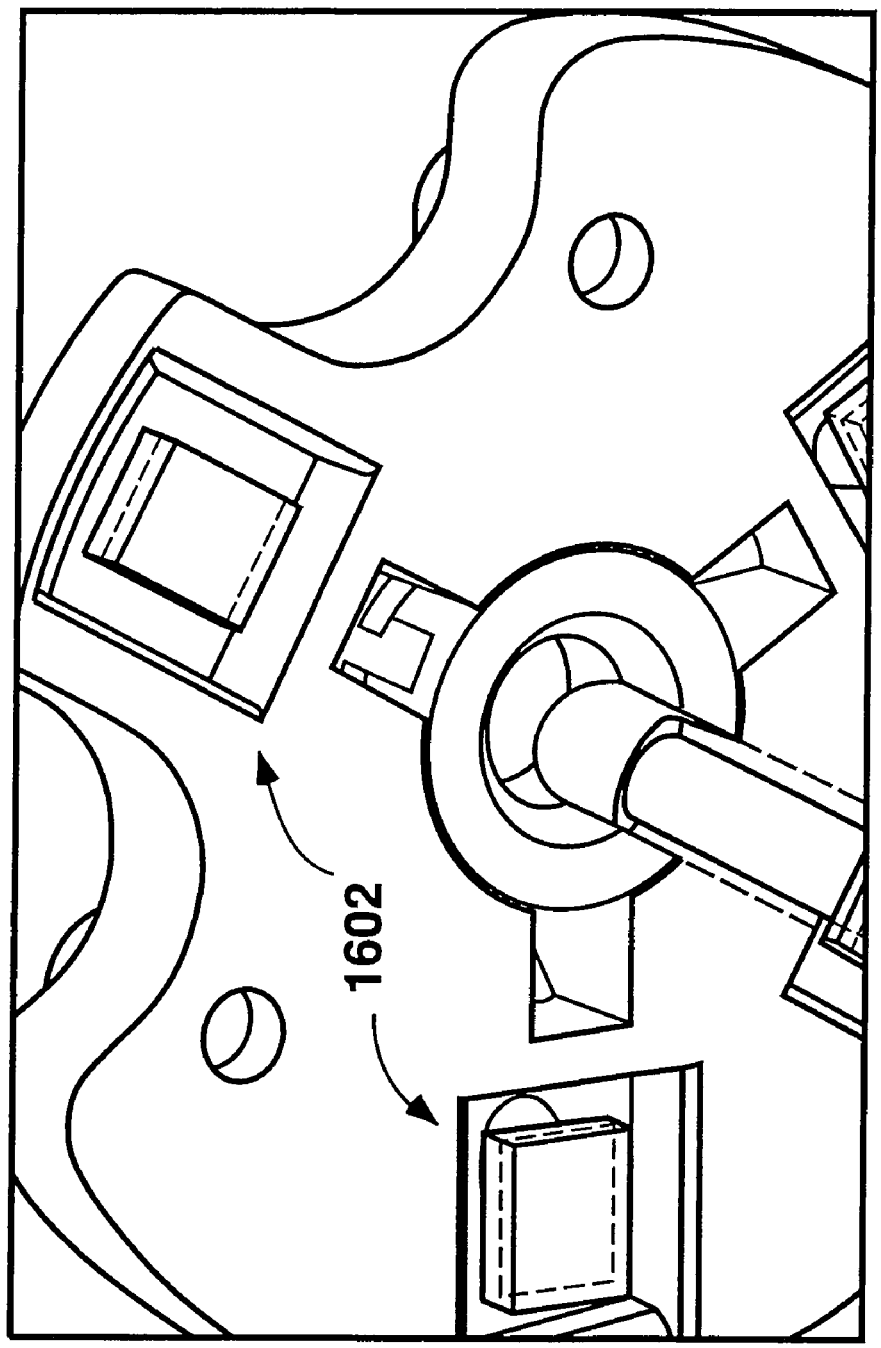
FIG. 16 shows various sensors according to various embodiments of the present invention.

The receiver optics 914 may include one or more sensors 915 positioned along discrete reflectance directions. In various embodiments, the sensors 915 may be positioned to sense non-coplanar reflectance directions such as, for example, reflectance directions 206, 208 and 210 shown in FIG. 2. The sensors 915 may be any kind of imaging or non-imaging sensor or sensor assembly suitable for measuring reflectance (e.g., across multiple discrete wavelength ranges). For example, the sensors 915 may include one or more photodiodes. Any suitable kind of wavelength discriminating equipment (e.g., any kind of band-pass spectral filter, diffraction grating spectrograph, etc.) may be placed in front of the photodiode to sense discrete wavelength ranges. For example, the MAZet Jencolour product line may be used, as shown by sensors 1602 in FIG. 16. In various embodiments, a wheel or other movable device including multiple band-pass filters may be selectively placed in front of the photodiode, allowing one photodiode to measure several discrete wavelength ranges. In other various embodiments, multiple photodiodes may be provided along each reflectance direction, which each of the multiple photodiodes having a separate band-pass filter. It will be appreciated that the sensors 915 may include a wide-band detector capable of discretely measuring multiple wavelength ranges simultaneously such as, for example, a RGB sensor, such as a camera with a logarithmic response or a small array of pixels (e.g., the TCS230 line available from Taos, Inc.).

Figure 10:
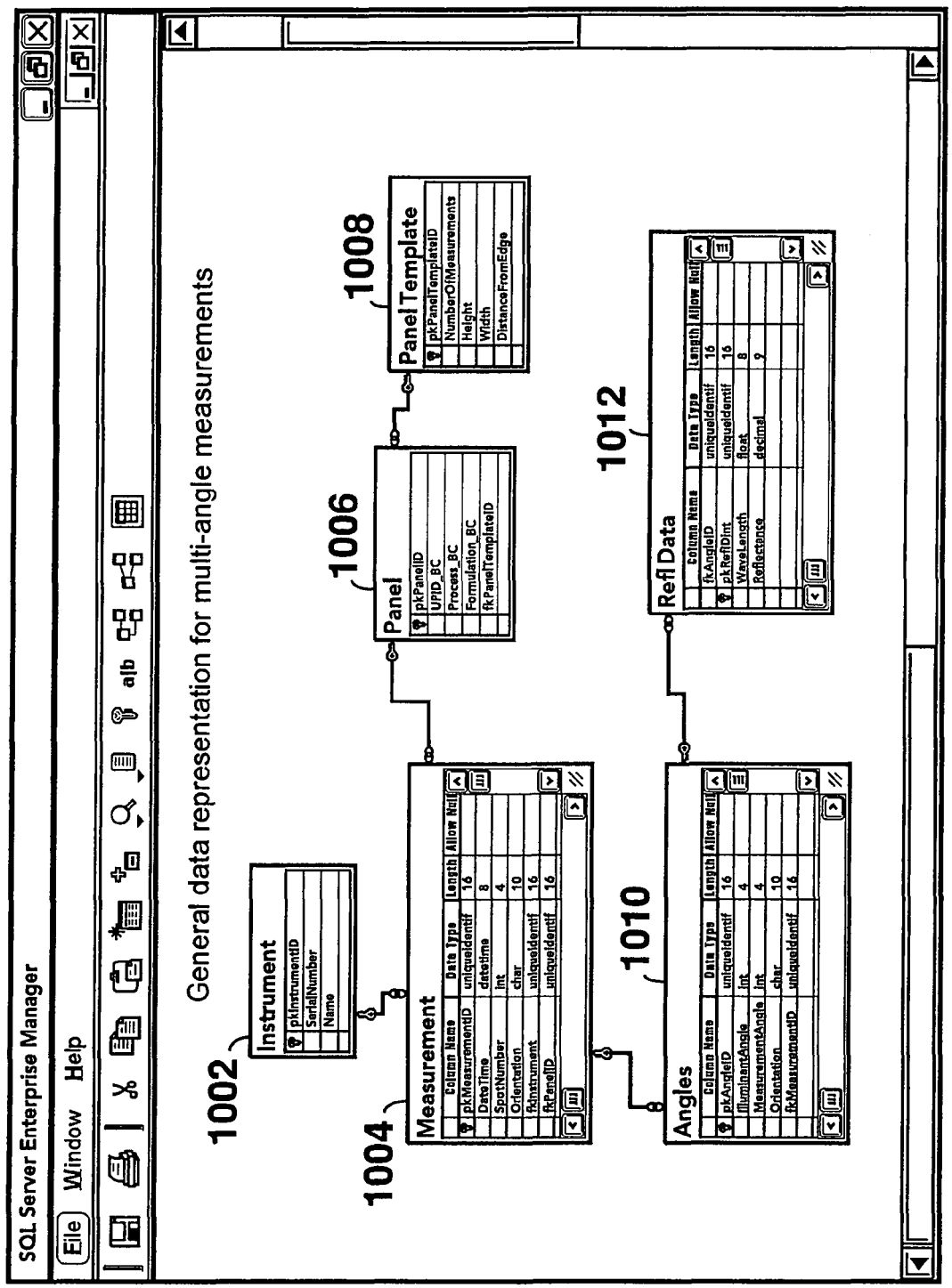
FIG. 10 shows a user interface that may be presented to a user according to various embodiments of the present invention.
Figure 11:
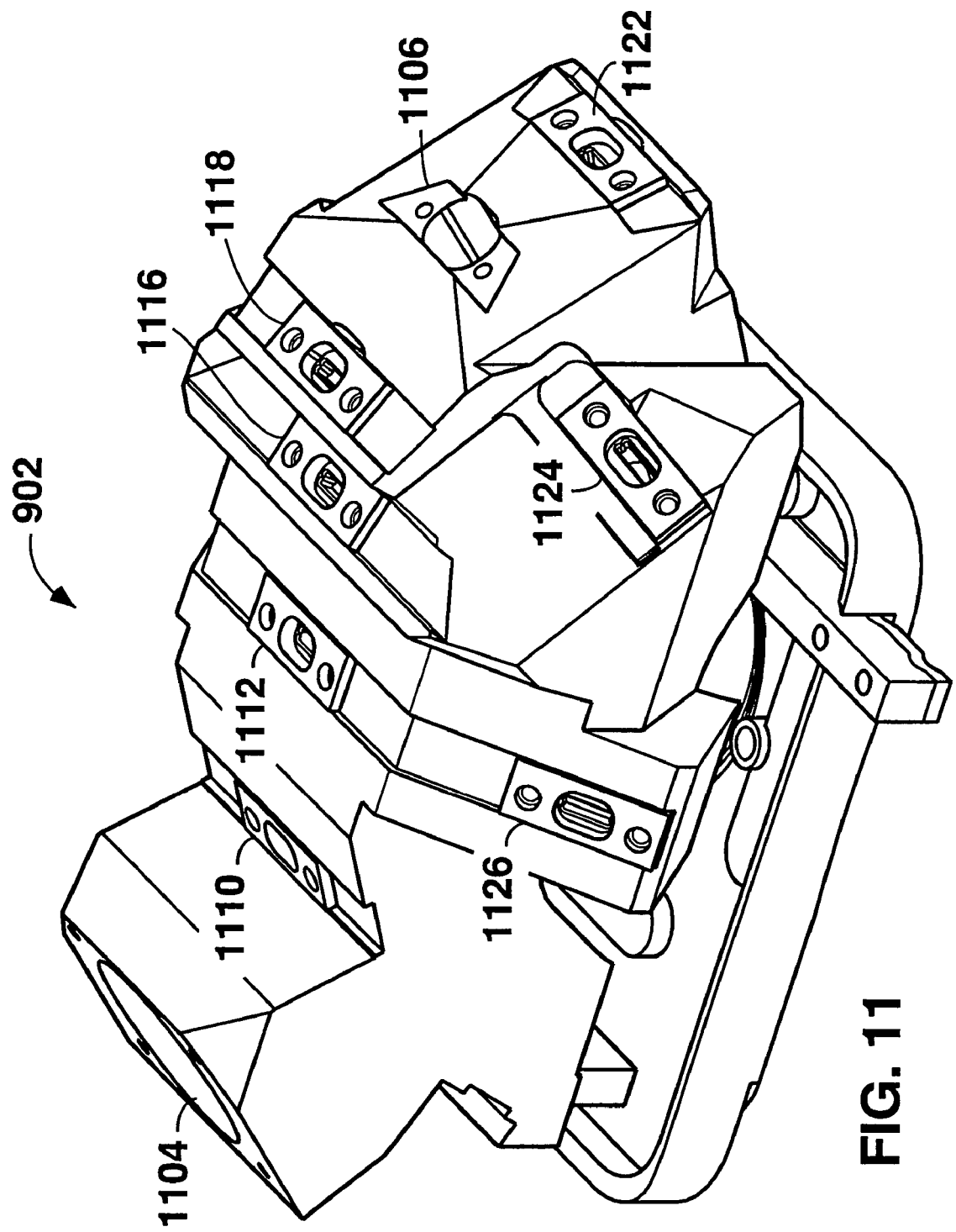
FIGS. 11-14 shows three-dimensional views of an apparatus according to various embodiments of the present invention.
Figure 12:
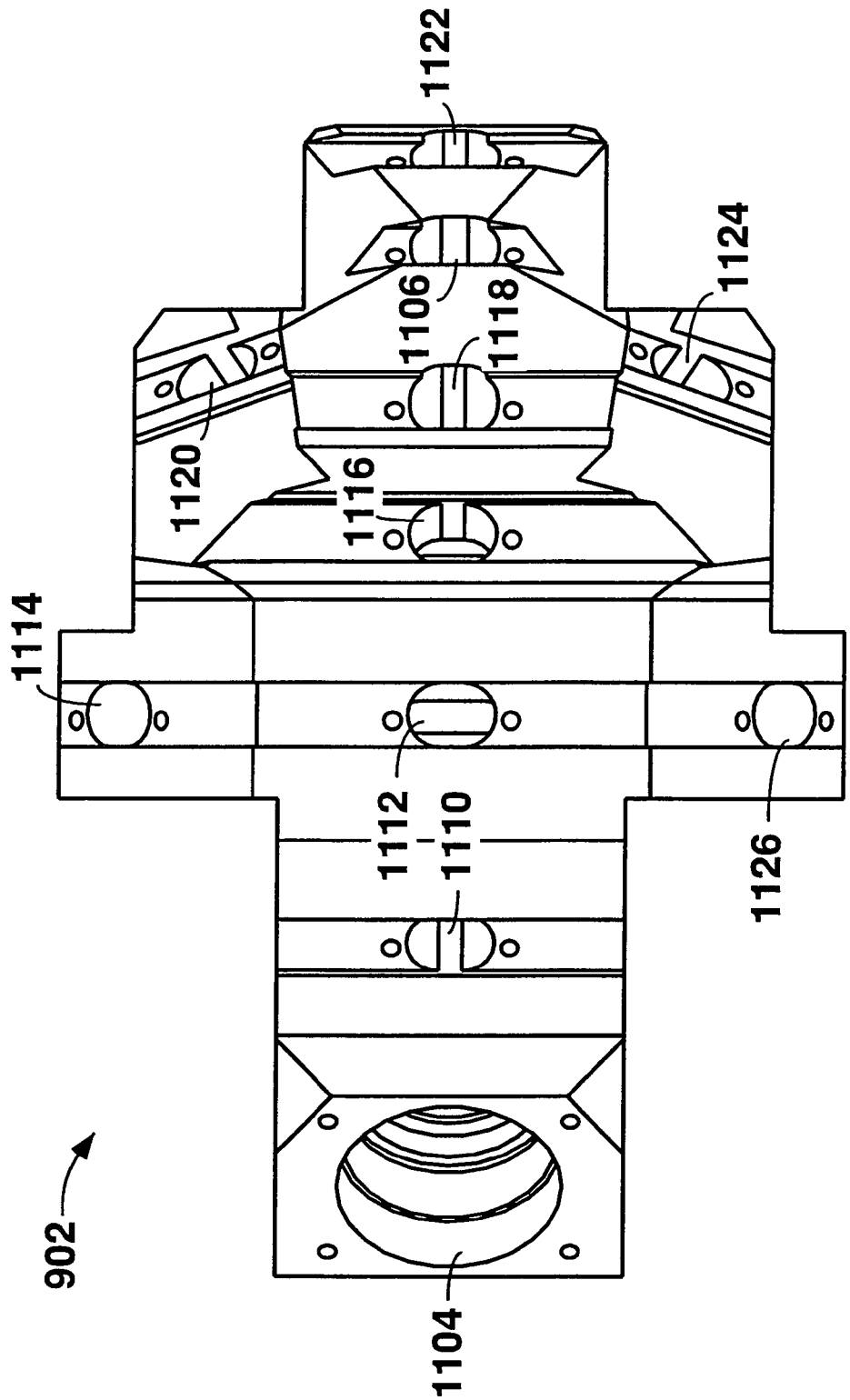
Figure 13:
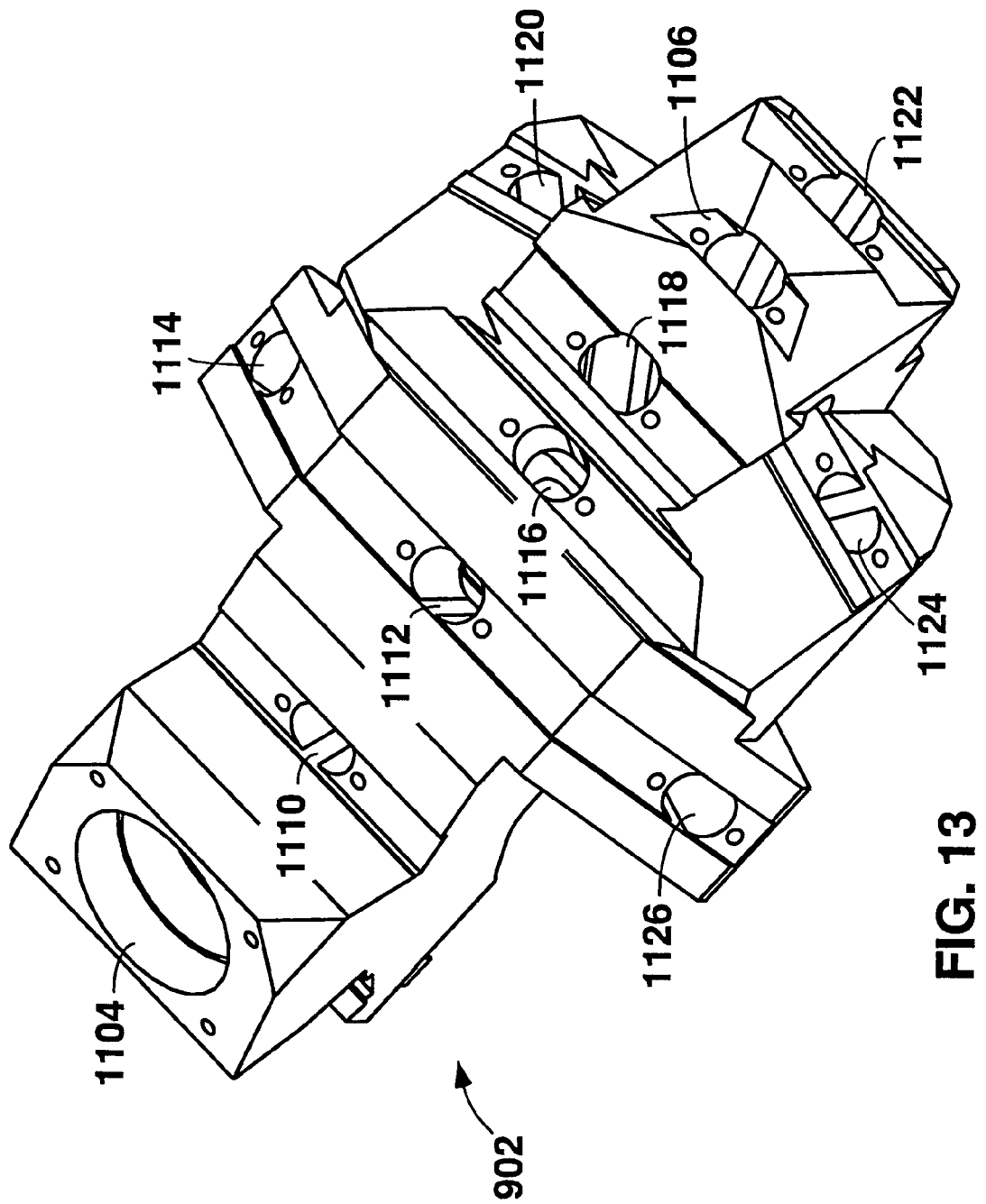
Figure 14:
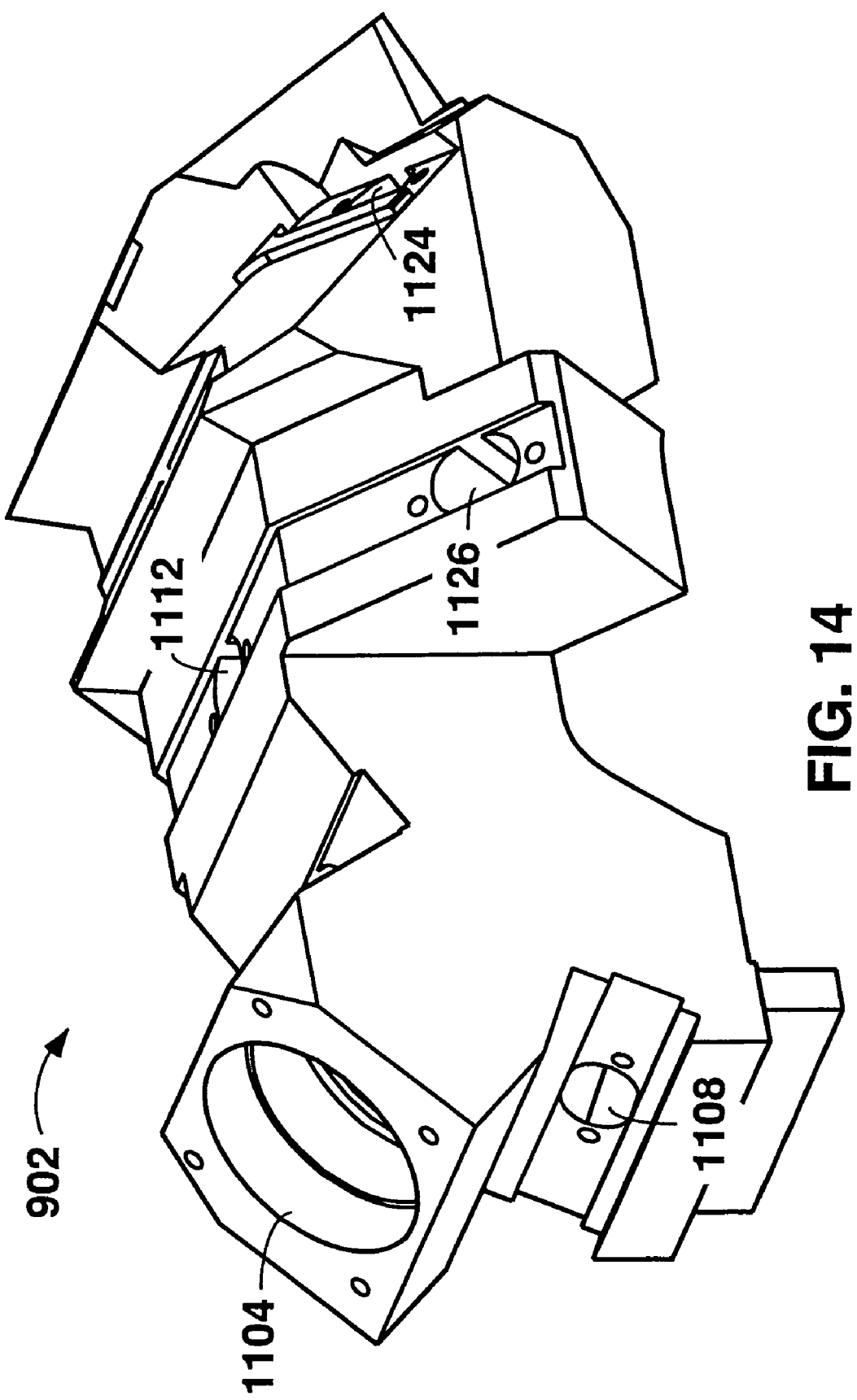

FIG. 10 shows an exemplary database schema 1000 that may be used to store measurement data, for example, at database 924 and/or electronics unit 904. Box 1002 may include information about the instrument (e.g., instrument 900) that is taking the measurement. Such information can include a name, serial number, etc. Box 1004 may include information about a particular measurement including, for example, date, time, location number, instrument orientation, etc. Boxes 1006 and 1008 may include information about the panel or surface under measurement. For example, box 1006 may include information about the panel or surface itself while box 1008 may include a template of preferred measurements to be taken on the surface (e.g., the number, height, width, distance from the edge, etc.). Box 1010 may include information about each of the angles or reflectance directions that are to be observed, and box 1012 may include actual measured data. For example, if eleven reflectance directions are measured over thirty-one wavelength ranges, then the total number of data points for each measurement may be 341.

FIGS. 11-14 show views of an exemplary optics unit 902 according to various embodiments. The exemplary optics unit 902 includes one illumination source 1104 and eleven apertures or pupils for receiving sensors 1106, 1108, 1110, 1112, 1114, 1116, 1118, 1120, 1122, 1124, 1126. It will be appreciated that sensor may comprise an aperture for receiving light and a receiving element for sensing the intensity of the light. In the exemplary unit 902, the illumination source 1104 is directed toward a surface positioned below the unit (not shown) at a forty-five degree angle relative to the surface normal. Accordingly, the specular reflectance direction is also at a forty-five degree angle relative to the surface normal. Pupil 1106 may be positioned to sense reflectance at the specular reflectance direction.

In various embodiments, the positions of the other pupils may be expressed relative to the specular reflectance direction, although, it will be appreciated that the positions of the pupils may be expressed in any suitable coordinate system. For example, pupil 1122 may be positioned at −15° relative to the specular. Pupil 1118 may be at 15° relative to the specular, with pupil 1116 at 25°, pupil 1112 at 45°, pupil 1110 at 75°, and pupil 1108 at 110°. The location of pupils off the plane of pupils 1106, 1108, 1110, 1112, 1116, and 1118 may also be expressed relative to the specular reflectance direction. For example, pupil 1124 is positioned 25° from the specular reflectance direction and rotated 90° counterclockwise out of plane. Similarly, pupil 1120 is positioned 25° from the specular reflectance direction and rotated 90° clockwise out of plane. Pupils 1114 and 1126 are both positioned 60° from the specular reflectance direction and rotated 54.7° clockwise and counterclockwise out of plane, respectively.

Figure 15:
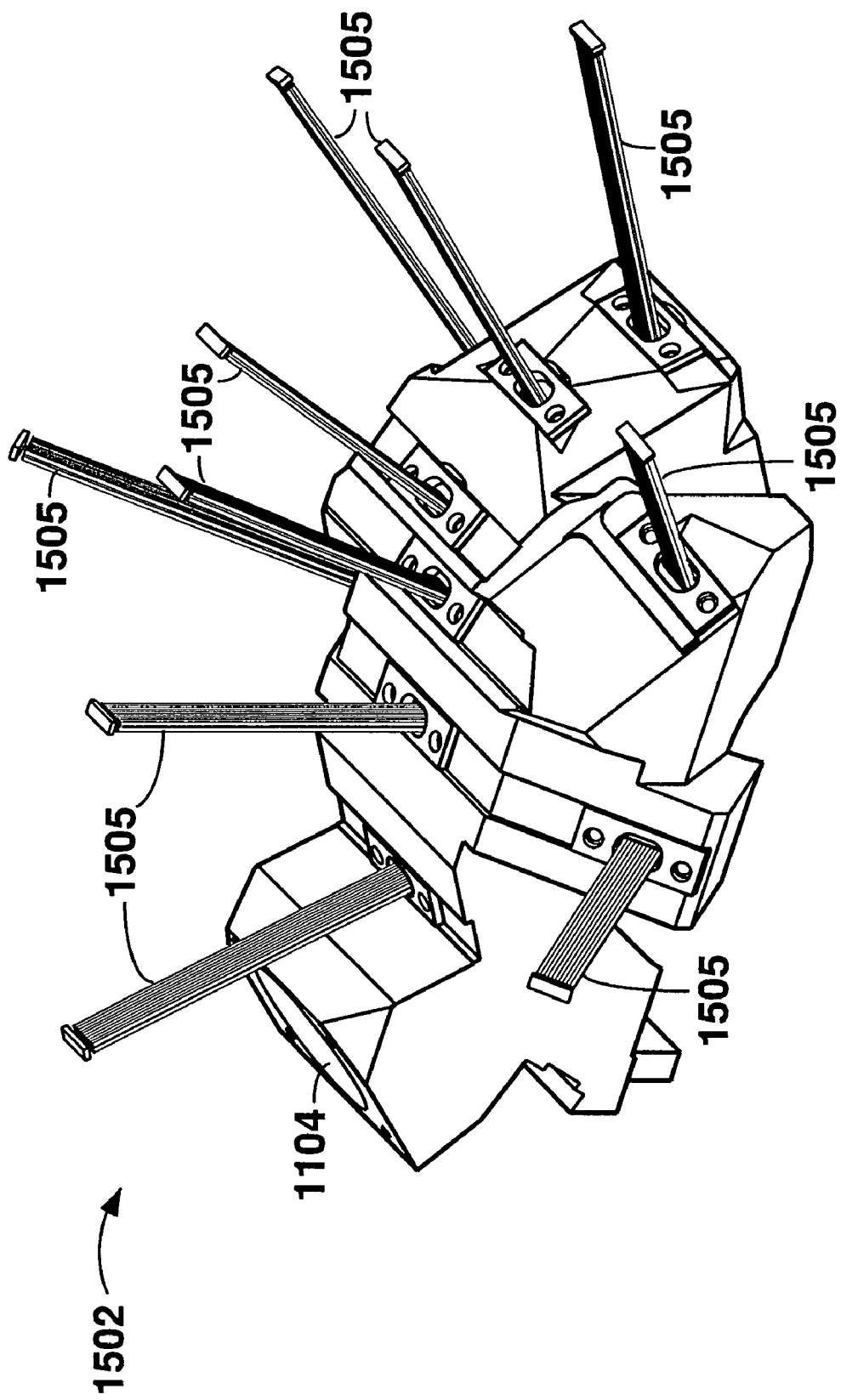
FIG. 15 shows a three-dimensional view of an apparatus according to various embodiments of the present invention.

It will be appreciated that although eleven pupils for sensors are shown, any suitable number of sensors may be used. Also the sensors may be placed to receive any suitable reflectance directions, for example, reflectance directions that are non-coplanar. Also, in various embodiments, the sensors may be positioned at in the various pupils of the optics unit 902. In other various embodiments, some or all of the sensors may be positioned remote from the pupils. For example, FIG. 15 shows another exemplary optics unit 1502 having optical fibers 1505 originating at various pupils. The fibers 1505 may transport light incident at the pupils to a remote location (not shown) that may house one or more receiving elements.

FIG. 17 shows an exemplary process flow 1700 for identifying properties of an unknown surface using the methods and/or apparatuses described above. At steps 1702, 1704, 1706, and 1708, various appearance properties may be derived from the observed reflectance or BRDF of the surface. For example, at step 1704, a magnitude of the weighted spectral spatial distribution may be found. At step 1704, an integrated BRDF of the surface may be found. An integrated BSDF of the surface may be found at step 1706. In various embodiments, a grating line structure of the surface may be found at step 1708. At step 1710, the appearance properties are compared to a look-up table, such as look-up Table 1, below to identify the unknown surface and/or physical properties thereof. It will be appreciated that the look-up table may be stored, for example, by the database 924 and/or the electronics unit 904 of the device 900.

TABLE 1

| Surface Type | Weighted Spectral Spatial Distribution Magnitude | Integrated BRDF | Integrated BSDF | Grating Structure Line | Moment Size | Diffuse/ Specular |
|---|---|---|---|---|---|---|
| Specular Absorber | Small | Small | Small | N/A | N/A | Specular |
| Pigmented Surface | Small | Small | Large | N/A | Medium | N/A |
| Surface Texture Absorber | Small | Small | Large | N/A | Small | N/A |
| Specular Pure Absorber | Small | Large | Small | N/A | N/A | N/A |
| Heavy Surface Structure | Large | Small | Small | Yes | N/A | N/A |
| Metal Flake | Large | Small | Large | No | N/A | N/A |
| Special Effect - Chroma Flair | Large | Small | Large | Yes | N/A | N/A |
| Special Effect - Mica | Large | Large | Small | No | N/A | N/A |
| Surface Scratches | Large | Large | Small | Yes | N/A | N/A |
| Special Effect - Chroma Flair | Large | Large | Large | Yes | N/A | N/A |
| Potential Calibration Error | Large | Large | Large | No | N/A | N/A |
| Potential Calibration Error | Small | Small | Small | N/A | N/A | Diffuse |
| Potential Calibration Error | Small | Large | Large | N/A | N/A | N/A |
| Undetermined | Large | Small | Small | No | N/A | N/A |

FIG. 18 shows a process flow 1800 for using the processes and/or apparatuses described above to find a directional color difference between two surfaces according to various embodiments. In the process flow 1800, the directional color difference is a Delta E value computed according to the CIELAB equations, though it will be appreciated that any suitable color measurement methodology may be used. At step 1802, an XYZ weight matrix may be computed based on a specified illuminant and observer. The XYZ weight matrix may be of size 3 by X, where X is the number of discrete wavelengths or wavelength range that are measured. Recall that the weighted directional response can be represented by a set of vectors, with one vector for each wavelength range. Accordingly, the weighted directional response may be represented as a vector of size X by d, where d is the number of terms necessary to represent the spatial coordinate axis (e.g., in three dimensions, d is equal to 3). The two matrices may be multiplied at step 1804 resulting in a 3 by d matrix. The CIELAB functions may be applied at step 1806. In various embodiments, the CIELAB functions may be applied to each column of the 3 by d matrix individually. Alternatively, the CIELAB functions may be applied to the magnitude of each column of the 3 by d matrix. At step 1808, the Delta E value may be calculated.

Figures 19, 20:
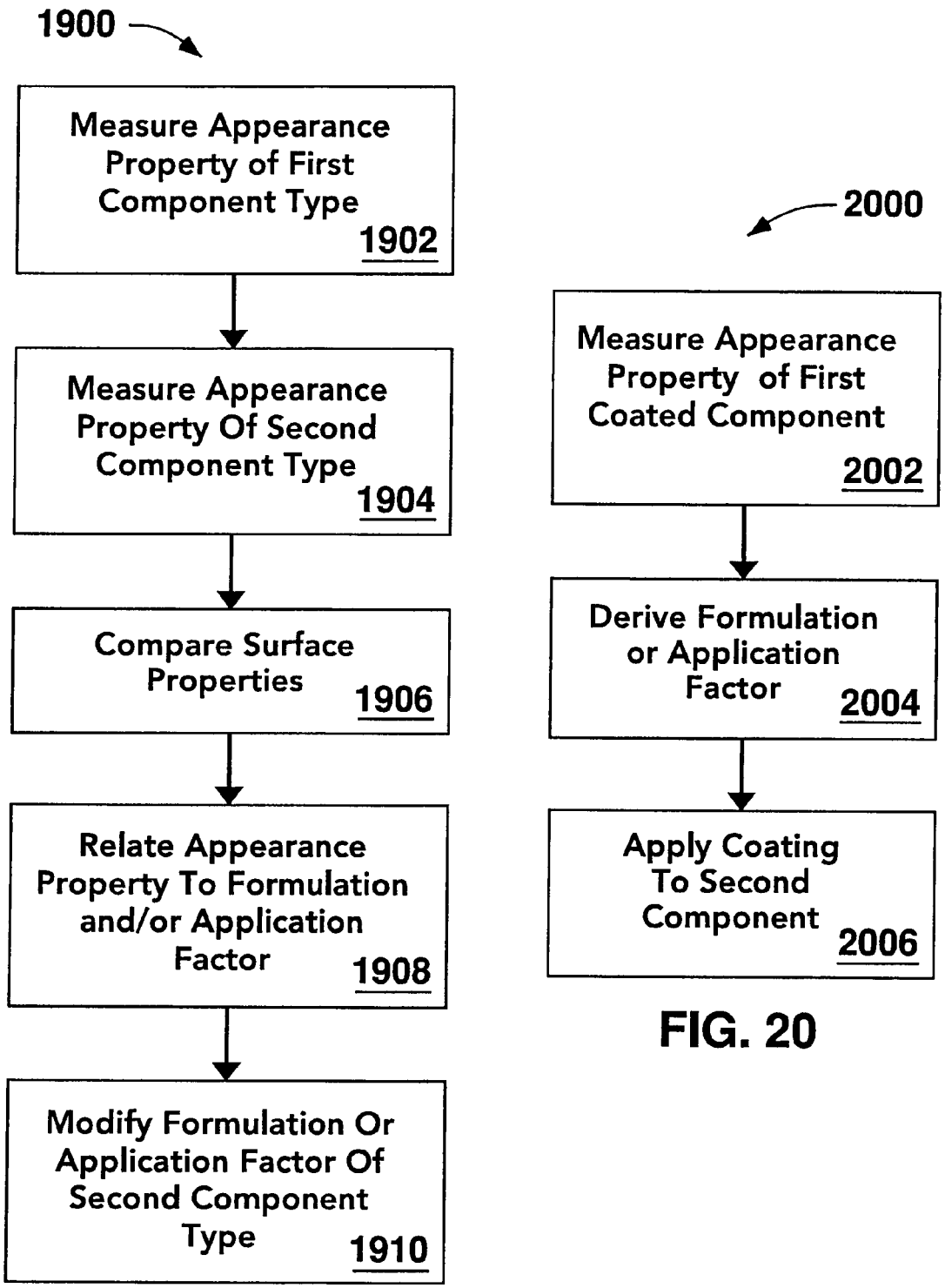

FIG. 19 shows a process flow 1900 that may be utilized in the coatings industry, for example, by a finisher of automotive parts, to match the appearance of coatings applied to two components, which may be manufactured and coated at different times and different facilities (e.g., a door handle may be made at Factory A, while a bumper may be made at Factory B). The process flow 1900 may be used to determine coating formulation and/or process factors for the second component based on observations of the first component. At step 1902, an appearance property of a first coated component may be measured and/or calculated. The appearance property may be, for example, a weighted directional response, BRDF, etc. At step 1904, an appearance property of a second coated component may be measured, for example in the same way as the first. At step 1906, the appearance properties of the two coated components may be compared. If differences are found, (e.g., because the second coated component does not match the first) then the appearance property exhibiting the differences may be tied to a particular formulation or application factor at step 1908, for example, as described above. The formulation or application factor of the second coated component may then be modified, at step 1910, to coat additional components to match the first, allowing a higher quality appearance match between components.

FIG. 20 shows a process flow 2000 for determining process and/or formulation factors to be used when coating a replacement part. At step 2002, an appearance property of a first coated component may be found (e.g., a weighted directional response, BRDF, etc.). The first coated component may be, for example, a component of an automobile. At step 2004, a formulation or application factor for reproducing the appearance of the coating on the first component may be found (e.g., by tying the appearance property to the formulation or application factor). At step 2006, a coating may be applied to a second component, considering the formulation or application factor found at step 2004. The process flow 2000 may be useful, for example, to autobody shops. In this way the coating of the second component may match that of the first. Using the process flow 2000, an autobody shop may match the paint formulation and process used to repaint a component or paint a replacement component to match the appearance of components already on the car. This may provide a better appearance match then reproducing the original formulation and process factors, as the appearance of the components changes with weathering and wear.

Figures 21, 22:
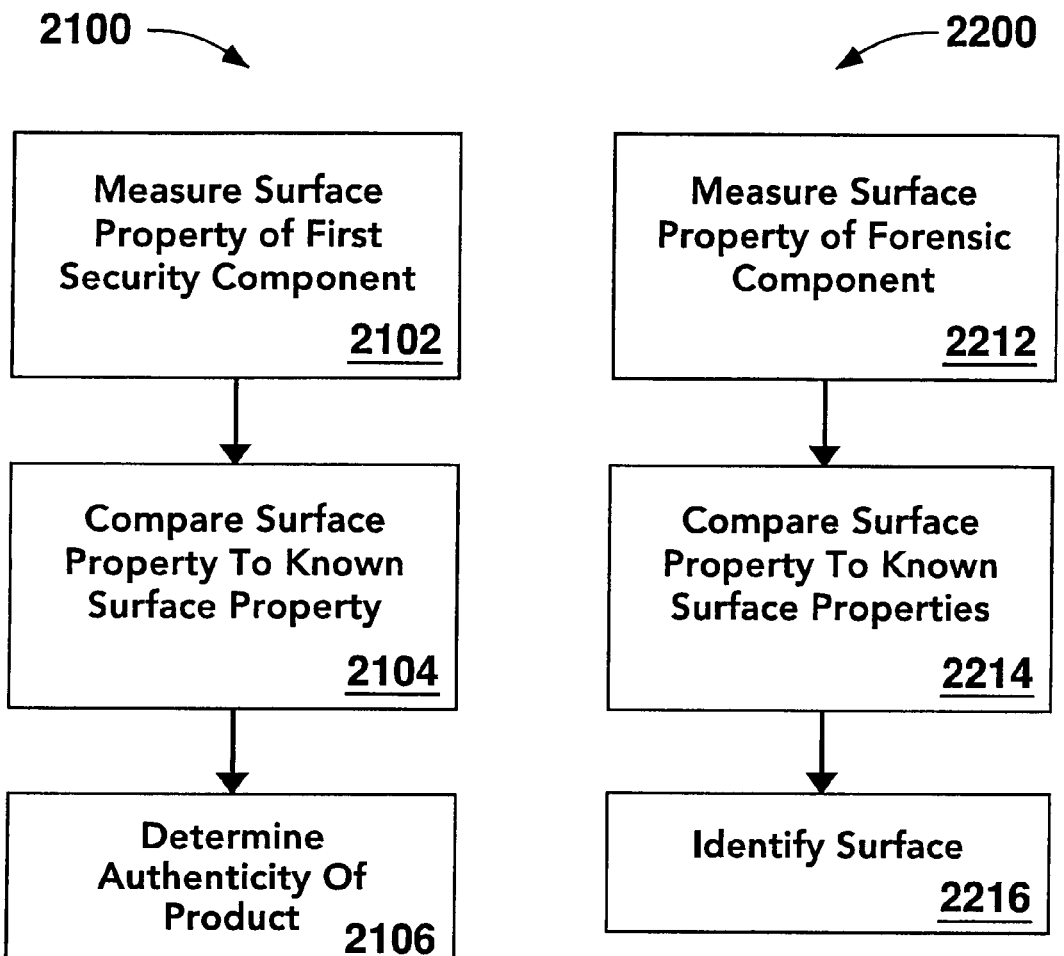

FIG. 21 shows a process flow 2100, according to various embodiments, for verifying the identity of a security component. The security component may be, for example, a security ink (e.g., a security ink having an appearance that depends on viewing angle). The ink may be present on a label or other indicator on a product. In various embodiments, the security component may be the product itself, for example, in the instance of a cosmetic or similar product having a distinct appearance. Referring to the process flow 2100, at step 2102, an appearance property of the first unknown component may be measured. The appearance property may be a weighted directional response, BDRF, etc. At step 2104, the measured appearance property may be compared to a known appearance property of an authentic security component. The authenticity of the product under test may be found at step 2106. For example, if the appearance property of the unknown security component matches the appearance property of the known product, then the unknown product is likely authentic. If the property of the tested security component does not match the known property, then the product may be counterfeit. It will be appreciated that the reliability of the match may be increased by considering multiple independent appearance properties.

FIG. 22 shows a process flow 2200 according to various embodiments, for identifying the source of a component. The process flow 2200 may be useful, for example, to forensic investigations. At step 2212, an appearance property of a component may be analyzed. The component may be, for example, an automobile body piece at the scene of a hit and run accident, a scrap of clothing left at the scene of a crime, or other component that is the subject of a forensic investigation. At step 2214, the appearance property of the component may be compared to similar properties of components of known origins. At step 2216, the component may be identified based on a match between the measured appearance property and the known appearance properties. For example, an automobile body piece may be tied to a particular make, model, production run, etc.

According to exemplary embodiments of the present disclosure, digital numerical analysis (DNA) may be employed to summarize and/or transform multiangle spectral data into a two or three dimensional spectral representation. DNA processing may be (−0.42, 0.00, 0.91), (0, 0.42, 0.91), (0.42, 0.00, 0.91), (0, 0.71, 0.71), (−0.71, 0.50, 0.50), (0.71, 0.50, 0.50), (0, 0.97, 0.26), and (0, 0.94, −0.34), respectively.

The following Table 2 shows spectra and corresponding DNA coordinates for a hypothetical measured sample. Using the coordinates of the direction vectors set forth in the previous paragraph, the z coordinate is computed at 700 nm is 213*0.97+47.5*0.97+17*0.91+13.7*0.91+14.6*0.91+ 2.1*0.71+0.9*0.50+0.9*0.50+0.9*0.26+0.9*−0.34=39.5. The exemplary embodiment of Table 1 includes measurements at sixteen (16) wavelengths. Greater (e.g., 31) or lesser measurement wavelengths may be employed according to the present disclosure to generate an appropriate fingerprint.

TABLE 2

|  | 45as-15az0 | 45as15az0 | 45as25az-90 | 45as25az0 | 45as25az90 | 45as45az0 | 45as60az-54.7 |
|---|---|---|---|---|---|---|---|
| 400 | 34.1 | 98.5 | 8.1 | 43.2 | 6.9 | 4.8 | 1.5 |
| 410 | 28.6 | 75.9 | 5.4 | 40.9 | 4.8 | 6.5 | 1.5 |
| 420 | 33.4 | 49.6 | 4 | 30.9 | 3.5 | 7.2 | 1.3 |
| 430 | 49.1 | 31.3 | 3.5 | 21 | 3.2 | 6.6 | 1.1 |
| 440 | 75.5 | 21.4 | 4.2 | 13.9 | 3.7 | 5.2 | 0.9 |
| 450 | 113 | 18.1 | 5.8 | 9.8 | 5.1 | 3.8 | 0.8 |
| 460 | 154 | 21.1 | 8.5 | 8.3 | 7.4 | 2.9 | 0.8 |
| 470 | 185 | 29.8 | 12.1 | 9 | 10.4 | 2.3 | 0.8 |
| 480 | 197 | 44.7 | 16 | 11.9 | 13.6 | 2 | 0.9 |
| 490 | 185 | 67.3 | 19.2 | 17.5 | 16.4 | 2.1 | 1 |
| 500 | 158 | 93.6 | 20.4 | 25.9 | 17.4 | 2.4 | 1.1 |
| 510 | 128 | 118 | 19.4 | 36.2 | 16.5 | 3.1 | 1.3 |
| 520 | 99.4 | 133 | 17.1 | 46.6 | 14.5 | 4.2 | 1.5 |
| 530 | 77.6 | 131 | 14.3 | 53.1 | 12.1 | 5.7 | 1.6 |
| 540 | 60.6 | 120 | 11.6 | 54.3 | 9.8 | 7.1 | 1.6 |
| 550 | 46.8 | 101 | 9.3 | 50.7 | 7.9 | 8.3 | 1.6 |
| 560 | 37.4 | 82.6 | 7.5 | 44.1 | 6.4 | 8.7 | 1.4 |

TABLE 2-continued

| | | | | | | | |
|---|---|---|---|---|---|---|---|
| 570 | 31.2 | 67 | 6.1 | 37 | 5.2 | 8.5 | 1.3 |
| 580 | 27.8 | 53.8 | 5.1 | 30.5 | 4.4 | 7.7 | 1.1 |
| 590 | 27 | 43.1 | 4.3 | 24.8 | 3.7 | 6.7 | 1 |
| 600 | 29.2 | 34.8 | 3.8 | 20.2 | 3.3 | 5.8 | 0.9 |
| 610 | 35.2 | 28.3 | 3.7 | 16.5 | 3.2 | 4.9 | 0.8 |
| 620 | 44.9 | 23.8 | 3.7 | 13.7 | 3.3 | 4.2 | 0.7 |
| 630 | 58.6 | 20.7 | 4.1 | 11.6 | 3.6 | 3.6 | 0.7 |
| 640 | 76.1 | 18.4 | 4.8 | 9.8 | 4.2 | 3.1 | 0.7 |
| 650 | 98.5 | 18.5 | 6 | 8.8 | 5.2 | 2.7 | 0.7 |
| 660 | 124 | 20.2 | 7.5 | 8.4 | 6.6 | 2.4 | 0.7 |
| 670 | 151 | 24 | 9.5 | 8.7 | 8.3 | 2.2 | 0.7 |
| 680 | 175 | 29.6 | 11.7 | 9.6 | 10.2 | 2.1 | 0.8 |
| 690 | 194 | 37.5 | 14.1 | 11.3 | 12.2 | 2 | 0.8 |
| 700 | 213 | 47.5 | 17 | 13.7 | 14.6 | 2.1 | 0.9 |

| | 45as60az54.7 | 45as75az0 | 45as110az0 | x | y | z |
|---|---|---|---|---|---|---|
| 400 | 1.4 | 1.3 | 1 | −0.1 | 5.6 | 24.9 |
| 410 | 1.4 | 1.5 | 1 | 0.0 | 5.1 | 20.6 |
| 420 | 1.3 | 1.7 | 1 | 0.0 | 3.5 | 16.3 |
| 430 | 1.1 | 1.8 | 1 | 0.0 | 1.7 | 14.6 |
| 440 | 0.9 | 1.7 | 1 | 0.0 | −0.1 | 15.8 |
| 450 | 0.8 | 1.5 | 1 | 0.0 | −1.9 | 19.9 |
| 460 | 0.8 | 1.3 | 0.9 | −0.1 | −3.5 | 25.9 |
| 470 | 0.8 | 1.1 | 0.9 | −0.1 | −4.3 | 31.9 |
| 480 | 0.9 | 1 | 0.9 | −0.1 | −4.1 | 36.6 |
| 490 | 1 | 1 | 0.9 | −0.2 | −2.5 | 39.5 |
| 500 | 1.1 | 1.1 | 0.9 | −0.2 | −0.2 | 40.7 |
| 510 | 1.2 | 1.1 | 0.9 | −0.2 | 2.4 | 41.0 |
| 520 | 1.4 | 1.2 | 0.9 | −0.2 | 4.7 | 40.2 |
| 530 | 1.5 | 1.4 | 0.9 | −0.1 | 5.9 | 37.5 |
| 540 | 1.5 | 1.5 | 0.9 | −0.1 | 6.3 | 33.4 |
| 550 | 1.5 | 1.7 | 0.9 | −0.1 | 6.1 | 28.4 |
| 560 | 1.4 | 1.9 | 0.9 | −0.1 | 5.4 | 23.6 |
| 570 | 1.2 | 1.9 | 0.9 | −0.1 | 4.7 | 19.6 |
| 580 | 1.1 | 1.8 | 0.9 | 0.0 | 3.9 | 16.3 |
| 590 | 1 | 1.7 | 0.9 | 0.0 | 3.1 | 13.8 |
| 600 | 0.9 | 1.6 | 0.9 | 0.0 | 2.3 | 12.3 |
| 610 | 0.8 | 1.4 | 0.8 | 0.0 | 1.5 | 11.6 |
| 620 | 0.7 | 1.3 | 0.8 | 0.0 | 0.8 | 11.9 |
| 630 | 0.7 | 1.1 | 0.8 | 0.0 | 0.0 | 13.0 |
| 640 | 0.7 | 1 | 0.8 | 0.0 | −0.8 | 14.9 |
| 650 | 0.7 | 1 | 0.8 | 0.0 | −1.7 | 17.9 |
| 660 | 0.7 | 0.9 | 0.8 | −0.1 | −2.6 | 21.7 |
| 670 | 0.7 | 0.9 | 0.8 | −0.1 | −3.4 | 26.1 |
| 680 | 0.8 | 0.9 | 0.9 | −0.1 | −4.0 | 30.6 |
| 690 | 0.8 | 0.9 | 0.9 | −0.1 | −4.3 | 34.9 |
| 700 | 0.9 | 0.9 | 0.9 | −0.1 | −4.4 | 39.5 |

Figure 23:
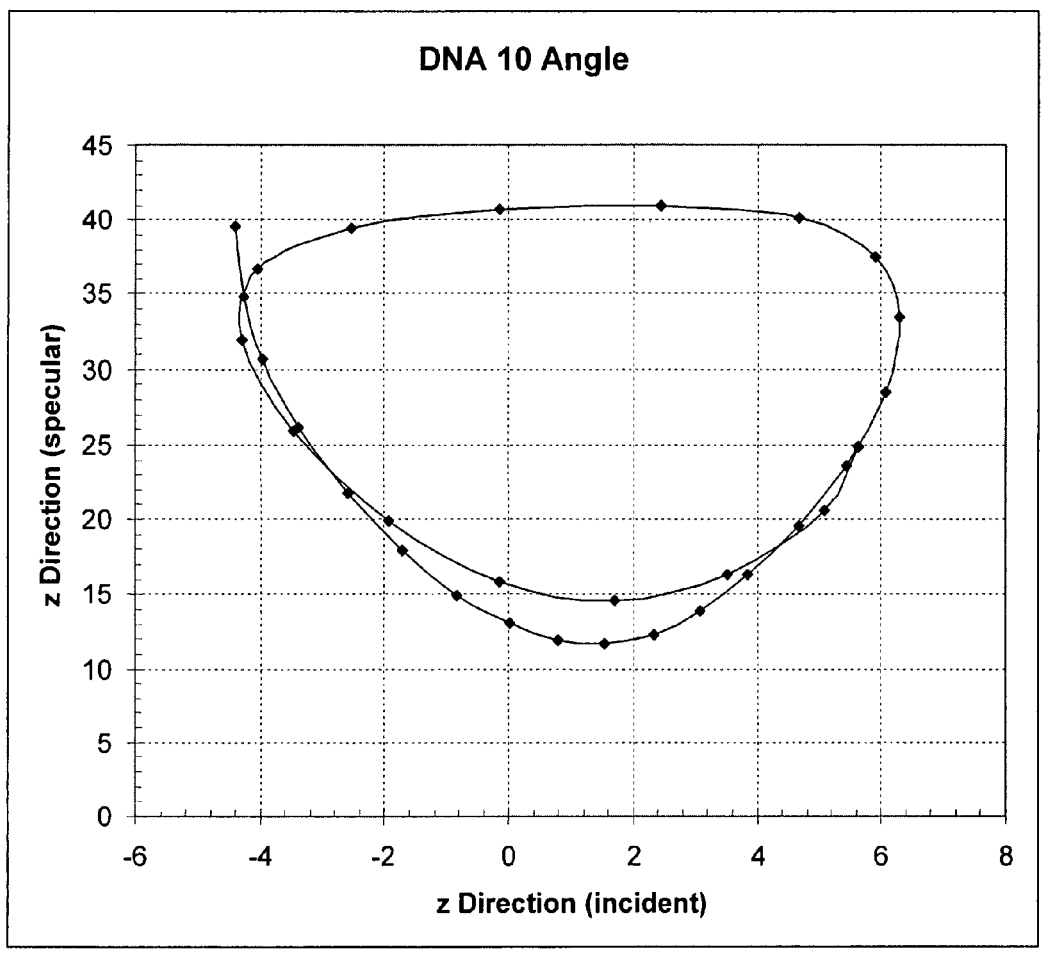
FIG. 23 is an exemplary (y,z) plot of a signature fingerprint for an exemplary surface according to the present disclosure.

A plot of the (y, z) projection based on the DNA coordinates for this hypothetical measured sample, i.e., a fingerprint for such measured sample is set forth in FIG. 23. Of note, any sample/substrate that exhibits the same (or substantially the same) plot will appear identical regardless of lighting, viewing angle, or other environmental conditions. Thus, the disclosed technique and associated systems facilitate matching of color/appearance based on appearance properties, as described herein.

The DNA spectrum disclosed herein incorporates two distinct principles for purposes of measuring, matching or otherwise using/accessing color properties. According to a visual principle, the disclosed DNA spectrum represents the color appearance of the measured surface at a given wavelength. By contrast, according to a structural appearance principle, the unique shape of the DNA spectrum represents the optical properties of the measured surface. In addition, the shape of the DNA spectra can be used to represent, assess and/or determine formulation characteristics. Of note, according to these principles, two samples having DNA spectra of the same shape, but a different position and orientation in space, will have a different color appearance. The difference in position and orientation of their DNA spectra represent process differences.

The disclosed DNA methodology is applicable to any multiangle geometry. The geometry required for measuring a particular class of materials generally depends on the physical properties of the samples to be measured. For example, diffuse materials can be accurately characterized with a single angle measurement. Typically, three positive aspecular angles may be sufficient to characterize coatings with metallic pigments. Adequate measurements of coatings with pearlescent and special effect pigments generally require additional angles beyond the traditional multiangle directions.

There are a number of goals, uses and/or purposes in transforming DNA spectra according to the present disclosure. These goals/uses/purposes include: (i) distinguishing process differences from formulation differences, (ii) monitoring process stability, and (iii) guiding process changes to compensate for normal variation(s) in coating formulation. As is known in the art, the separation between process and formulation is not entirely sharp. For example, additives such as fumed silica may be used to control metallic flake orientation in a coating. Since the index of refraction of fumed silica matches the index of refraction of common solvents, fumed silica is generally invisible except in its effect on flake orientation. Inasmuch as process variables (e.g., flow rate and atomization)

also affect flake orientation, the use of fumed silica is generally not distinguishable from process changes and/or variations.

To determine the equivalence of shapes of DNA spectra, exemplary implementations of the present disclosure employ linear operations of translation, rotation and scaling. With initial reference to the translation operation, translation of a DNA spectrum is based on the average 3D position over all wavelengths. The magnitude of translation may be denoted by xT, and the individual components are therefore denoted xTx, xTy, and xTz. The translation of a DNA spectrum to be centered at the origin is denoted DNAt.

Turning to the rotation operation, the rotation process generally includes three (3) rotations, performed in the following order:
1. A rotation in the xy plane (azimuth)
2. A rotation in the xz plane (colatitude)
3. A rotation in the yz plane (alignment)

The first two rotations are performed so that a best fit plane to the DNA spectrum is rotated to the yz plane. The noted rotations are typically computed based only upon the sample. The pair (azimuth, rotation) is denoted by xR. The rotation of the translated spectrum is denoted DNAt, and the first two rotations are denoted DNAr.

An alignment angle and scale factor are generally computed together using a least squares fit to minimize the distance between a sample DNA spectrum and a standard DNA spectrum. The alignment angle is denoted xA, and the scale factor is denoted xS. Although the alignment angle and the scale factor are computed together, they are generally applied separately. Rotation of the spectrum DNAr in the yz plane by the alignment angle is denoted DNAa, and the result of scaling the spectrum DNAa is denoted DNAs.

In implementing the disclosed systems and methods, care should be taken in determining when to use the aligned spectrum (DNAa) or scaled spectrum (DNAs). In some situations, two samples that differ only in process conditions have significant differences in their aligned spectra DNAa, so examination of the scaled spectra DNAs is needed and/or desired to determine that the difference between samples is indeed a process difference, not a formulation difference.

Of note, the DNA of a surface results from both the underlying material, characterized by DNAs, and its interaction with its environment, represented by application process conditions. In considering DNA transformations, the transformed spectra and the transformation parameters should be considered. In conventional applications, calorimetric values in use with multiangle measurements include Lab values per angle and Flop Index. As is known to persons skilled in the art, Flop Index is a measure of relative lightness change between near specular and near retro angles. The parameters xT, xA, and xS are related to the difference in reflectance at various angles, but they provide different views as compared to a Flop Index.

As an example, in a hypothetical situation a Flop Index of a coating containing metallic flakes can be reduced by coating application under dryer conditions and/or by using finer flakes in the coating. Such changes would more likely be detected by monitoring xT, xA, and xS, as compared to monitoring only the Flop Index. Of course, Flop Index remains a potentially useful tool. For example, multiangle measurements are useful with materials whose multiangle reflectances have multiple dimensions. No single number/parameter can capture all information of interest in such situations.

According to the present disclosure, useful calorimetric data can be advantageously derived from 3D DNA spectra. Among possible approaches to generalizing color difference formulae to higher dimensional spectra include:

1. Computation of calorimetric data, such as XYZ, LAB, and difference formulae on each of x, y, and z planes, and combination of difference formulae computed on the different planes as the square root of the sum of the squares of the single plane difference formulae. The color difference formula computed by generalizing ordinary Delta E may be is denoted dDNA.

2. Computation of XYZ data on each of x, y, and z planes. These values are used as the x,y,z components of vector-valued X, Y, and Z data. The magnitude of the three dimensional X, Y, and Z vectors is then computed, and the L, a, b and color difference data are computed using the one dimensional X, Y, and Z magnitudes.

3. When computing difference formula based on transformed spectra, it is generally advantageous to translate both standard and sample transformed spectra so as to be centered at the center of the standard's DNA spectrum before computing the difference formula. That is, both standard and sample spectra are translated by the standard's (xTx, xTy, xTz) vector. This accounts for the piecewise nature of the CIELAB functions, which are much more sensitive to differences at low reflectance than at high reflectance. The application of Delta E to the various transformed spectra may be denoted dDNAt, dDNAr, dDNAa, and dDNAs.

The application of color difference formula based on human perception may not be desirable or fully effective when considering transformed spectra. Accordingly, in exemplary implementations of the present disclosure, the measure dF, which is calculated as the square root of the sum of the squared distances between corresponding points on the two DNA spectra, is employed. The measure dF thus represents the ordinary Euclidean distance between spectra.

As is known by persons skilled in the art, a logarithmic scale is frequently used instead of a linear scale in reflectance measurements. Accordingly, the measure dG, which involves applying the following non-linear function (8):

$$f(r) = \begin{cases} r^{1/3} & \text{if } r > 0.009 \\ 13.8672 + 7.704r & \text{if } r \le 0.09 \end{cases} \quad (8)$$

to each reflectance, then applying the dF formula to the result. This function is similar to the non-linear function applied to XYZ values in the CIELAB formula. As with dDNA, dFt, dFr, dFa, dFs, dGt, dGr, dGa, and dGs may be used to denote the result of applying dF or dG to transformed DNA spectra, and plain dF and dG for the result of application to untransformed DNA spectra.

Since the above-noted difference formulae may be applied to untransformed or transformed DNA spectra, it is useful to assess which particular transformation has the greatest effect on the resulting difference formula values. To help in this analysis, the following functions may be used: ΔdDNA, ΔdF, and ΔdG. These functions do not represent a single measure, but any difference of measures. Thus, the ΔdDNAxy function (where x and y are any of the characters 's', 'a', 'r', 't', or 'v' appended to DNA) may be used. For example, ΔdDNAta=dDNAt−dDNAa, and ΔdGvs=dG−dGs ('v' is used for untransformed spectra).

To further assist persons of skill in the art in designing and implementing systems, apparatus and methods according to the present disclosure, additional information concerning exemplary quantitative and qualitative information that may be derived and/or computed using, in whole or in part, various statistics and values associated with the disclosed DNA methodology are provided herein below.

DNA Weighted Vector Summation

As noted above, the DNA vector sum is generally a sum of the detector direction vectors, scaled by the reflectance in each direction, as well as an additional weight factor in each direction. The optional weight can be used to restrict the vector sum to certain directions, to emphasize particular directions, and/or to correspond to the energy present in each direction. Often, the specular direction may be excluded from the DNA vector sum (or have an extraordinary scale factor) because the specular channel tends to measure with an extremely high reflectance, but with little color information. Generally, direction measurements and vector sums are generated with a single illuminator, but multiple illuminators may be employed without departing from the spirit or scope of the present disclosure. If data from different illuminators is combined in a single 3D DNA sum, the out-of-plane axes will be aligned. Surface normal vectors and/or specular vectors from the different illuminators' vectors may also be aligned when combining data from different illuminators. Alternatively, data from different illuminators may be combined in a higher dimensional plot because, inter alia, some colors, particularly those with strong interference pigments, have multiangle data that is effectively more than three dimensional, so that a 3D DNA sum would potentially lose valuable information. Of note, if the detector directions are all in-plane, the DNA sum will lie in a two-dimensional space.

To derive an exemplary DNA fingerprint in three dimensional space according to the present disclosure, equation (9) may be used:

$$DNA_\lambda = \sum_\mu R_{\lambda,\mu} \cdot w_\mu \cdot (\mu_x, \mu_y, \mu_z) \quad (9)$$

where R is the 31×m matrix of measured reflectance values (for 31 wavelength measurements), $R_{\lambda,\mu}$ is the reflectance at wavelength $\lambda$ and measurement direction $\mu$, $\mu_x$, $\mu_y$, and $\mu_z$ are the components of the measurement direction, where the z, y, and x components are the specular direction, the in-plane projection of the illuminator direction orthogonal to specular, and the out-of-plane direction, respectively, and $w_\mu$, is the additional weight in direction $\mu$.

The translation vector for a DNA curve is the sum over wavelengths of the DNA. This gives a translation vector $$(xTx, xTy, xTz) = \sum_\lambda DNA_\lambda$$

in 3D space. The translated DNA is DNAt=DNA−(xTx,xTy,xTz), and the norm of the translation vector is $$xT = \sqrt{xTx^2 + xTy^2 + xTz^2}.$$

The alignment of DNA curves is generally performed in two steps. First, the rotation angles are computed to align the best fit plane to the DNA curve with the yz-plane. These angles are the azimuth and colatitude. The second step is to simultaneously compute a rotation angle within the yz plane and a scale factor using least squares.

To minimize numerical instability in computing the best fit plane, it may be desirable to shift the DNAt curve away from the origin. The result of such shift may be called M, which may be computed with formula (10):

$$M = DNAt + (10,0,0). \quad (10)$$

The best fit plane to M satisfies an equation of the form $\vec{x} \cdot \vec{n} = k$, where $\vec{n}$ is the normal vector to the plane and k is a constant. Since M does not go through the origin, k is non-zero. Thus, M satisfies an equation of the form $M\vec{n} = k\vec{v}$, where $\vec{v} = [1\ 1\ \ldots\ 1]^T$. The normal vector $\vec{n}$ may then be computed to the best fit plane as the least squares solution to the foregoing equation; using the normal equations approach. The solution is based on the equation $M^T M \vec{n} = M^T \vec{v}$. Thereafter, $\vec{n}$ may be scaled so that it is a unit vector.

To compute the azimuth and colatitude from the normal vector, the following equations may be used:

$$\text{Azimuth} = \arctan 2(n_y, n_x) \quad (11)$$

$$\text{Colatitude} = \arctan 2(n_z, \sqrt{n_x^2 + n_y^2}) \quad (12)$$

The result of rotating DNAt by the azimuth and colatitude may be denoted DNAr. For an azimuth of $\alpha$ and colatitude of $\gamma$, the rotated curve may be computed as:

$$DNAr = DNAt \begin{bmatrix} \cos(\alpha) & \sin(\alpha) & 0 \\ -\sin(\alpha) & \cos(\alpha) & 0 \\ 0 & 0 & 1 \end{bmatrix} \begin{bmatrix} \cos(\gamma) & 0 & \sin(\gamma) \\ 0 & 1 & 0 \\ -\sin(\gamma) & 0 & \cos(\gamma) \end{bmatrix} \quad (13)$$

The in-plane alignment angle and scale factor are computed with reference to a standard. For a given DNAr curve, form the matrix $$P = \begin{bmatrix} DNAr_y & DNAr_z & J & Z \\ -DNAr_z & DNAr_y & Z & J \end{bmatrix},$$

where $DNAr_y$ and $DNAr_z$ are 31×1 vectors containing the y and z components of DNAr, respectively; J is the 31×1 vector of all 1's; and Z is the 31×1 vector of all 0's. The linear system $P_{sample}X = P_{standard}$ may then be solved to yield an in-plane alignment angle, which is $xA = \arctan 2(-X_{2,1}, X_{1,1})$, and the scale factor is $$xS = \sqrt{X_{1,1}^2 + X_{2,1}^2}.$$

The aligned DNA is $$DNAa = DNAr \begin{bmatrix} 1 & 0 & 0 \\ 0 & \cos(xA) & \sin(xA) \\ 0 & -\sin(xA) & \cos(xA) \end{bmatrix},$$

and the scaled DNA is DNAs=xS·DNA.

EMT is the relative power in the xy components of the DNA curve. Graphically, this may be presented directly, or weighted by the inverse wavelength squared to mimic a dispersion curve. If EMT refers to the weighted version, the unweighted version may be denoted by EMTn. The equations for computing such EMT values are:

$$EMTn_\lambda = \frac{\sqrt{DNA_{\lambda,x}^2 + DNA_{\lambda,y}^2}}{\sqrt{DNA_{\lambda,x}^2 + DNA_{\lambda,y}^2 + DNA_{\lambda,z}^2}} \quad (14)$$

$$EMT_\lambda = 16\pi^2 EMTn_\lambda / \lambda^2 \quad (15)$$

CIELAB, DE and DE94 values may be computed on each plane of the DNA curve, and then the planes may be combined to arrive at single L, a, b, and/or DE values based on the DNA curve. The single DE values may be denoted dDNA and such values may be computed on raw or transformed DNA curves. Delta dDNA values may also be computed based on the difference of different transformed dDNA values.

The first step in computing CIELAB data is generally to compute XYZ values based on a specified illuminant and a specified observer. In the case of 31 point data, this computation involves multiplication of a 3×31 weight matrix by a 31×1 vector to produce a 3×1 vector. The corresponding step when the spectral data is a DNA curve in 3-dimensional space is to multiply the weight matrix by the DNA curve, arranged as a 31×3 matrix, as shown in equation (16):

$$\begin{bmatrix} x_\lambda \\ y_\lambda \\ z_\lambda \end{bmatrix} xDNA = \begin{bmatrix} X_x & X_y & X_z \\ Y_x & Y_y & Y_z \\ Z_x & Z_y & Z_z \end{bmatrix} \quad (16)$$

The CIELAB functions may then be applied to the XYZ data of each column individually:

$$\begin{bmatrix} L_x & L_y & L_z \\ a_x & a_y & a_z \\ b_x & b_y & b_z \end{bmatrix} = \quad (17)$$

$$\begin{bmatrix} CIE\_L(X_x, Y_x, X_z) & CIE\_L(X_y, Y_y, Z_y) & CIE\_L(X_z, Y_z, Z_z) \\ CIE\_a(X_x, Y_x, X_z) & CIE\_a(X_y, Y_y, Z_y) & CIE\_a(X_z, Y_z, Z_z) \\ CIE\_b(X_x, Y_x, X_z) & CIE\_b(X_y, Y_y, Z_y) & CIE\_b(X_z, Y_z, Z_z) \end{bmatrix}$$

To compute dDNA between two measurements, the square root of the sum of the squares of the differences between the 3×3 vectors is computed according to equation (18):

$$dDNA = \sqrt{\begin{array}{c}(L_x - L'_x)^2 + (a_x - a'_x)^2 + (b_x - b'_x)^2 + (L_y - L'_y)^2 + \ldots + \\ (a_z - a'_z)^2 + (b_z - b'_z)^2\end{array}} \quad (18)$$

The DNA curve utilized in the above-noted computations may be the raw DNA curve, or one of the transformed curves DNAt, DNAr, DNAa, or DNAs. It is noted that dDNAt, dDNAr, dDNAa, and dDNAs are generally used for the results of computing dDNA on transformed curves.

For purposes of calculating DF, DG, Delta DF and Delta DG, the square root of the sum of squared differences of reflectance on DNA curves may be computed, without the perceptual weighting of CIELAB, giving:

$$DF = \sqrt{\begin{array}{c}\sum_\lambda (DNA_{\lambda,x} - DNA'_{\lambda,x})^2 + (DNA_{\lambda,y} - DNA'_{\lambda,y})^2 + \\ (DNA_{\lambda,z} - DNA'_{\lambda,z})^2\end{array}} \quad (19)$$

The noted values may also be computed on raw and transformed DNA curves, giving DFt, DFr, DFa, and DFs.

If the non-linear function $$f(r) = \begin{cases} r^{1/3} & \text{if } r > 0.009 \\ 13.8672 + 7.704r & \text{if } r \le 0.09 \end{cases}$$

is first applied to reflectance values, equation (20) results:

$$DG = \quad (20)$$
$$\sqrt{\begin{array}{c}\sum_\lambda (f(DNA_{\lambda,x}) - f(DNA'_{\lambda,x}))^2 + (f(DNA_{\lambda,y}) - f(DNA'_{\lambda,y}))^2 + \\ (f(DNA_{\lambda,z}) - f(DNA'_{\lambda,z}))^2\end{array}}$$

and DGt, DGr, DGa, and DGs may be used to denote the values computed from transformed curves.

The traditional DE, DE94 and DEp/DIN6175-2 formulae may be applied to each angle individually. It is noted that the aspecular angle is required for DIN 6175-2, and the absolute value of the designated aspecular angle (i.e., 15 for the −15 direction) may be used. The Flop Index is typically computed in a traditional manner using 15°, 45°, and 110° L values.

Figure 24:
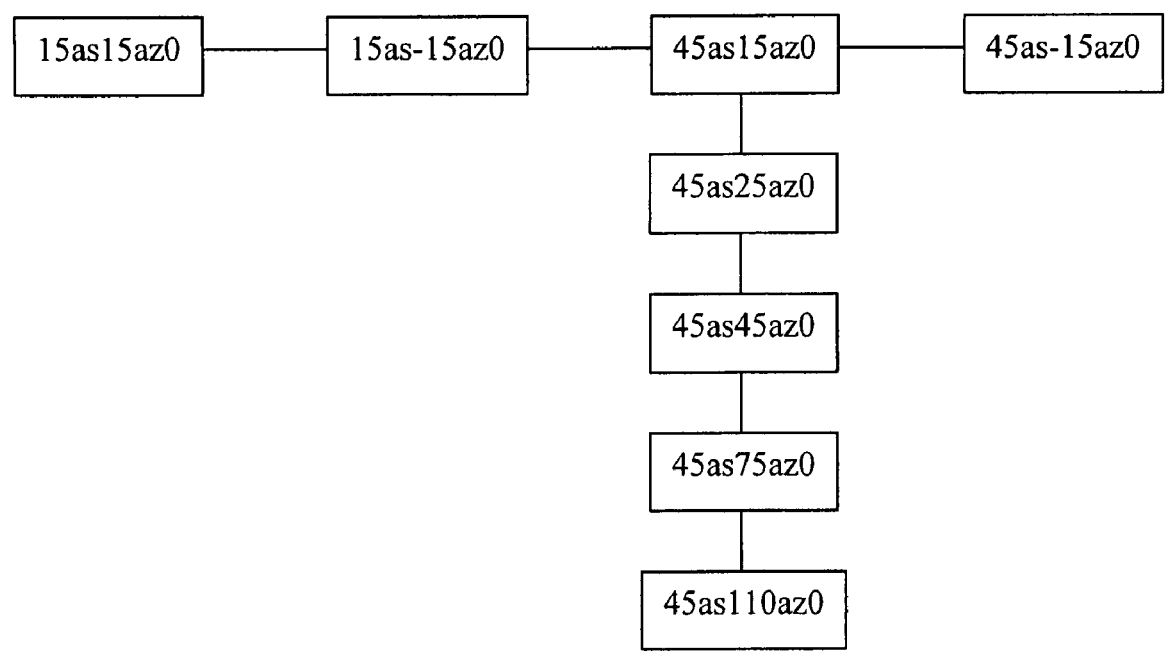
FIG. 24 is a chromaticity plot of per-angle value pairs showing the aspecular line and a rough approximation of the interference line for a surface according to the present disclosure.

As shown in FIG. 24, the per-angle (a*, b*) value pairs may be plotted for the 45° illuminator directions, and for the 15° illuminator, ±15° aspecular directions. The value pairs are connected in a 'T' shape, showing the aspecular line and a rough approximation of the interference line.

To further illustrate advantages and wide ranging applicability of the disclosed systems, apparatus and methods, reference is made to the following exemplary "use case scenarios." The present disclosure is neither limited by nor to the exemplary scenarios described herein. Rather, the exemplary "use case scenarios" presented herein are by way of example, and not limitation. As will be readily apparent to persons skilled in the art, the disclosed systems, apparatus and methods may be used and/or implemented in many alternative ways and environments.

Exempilar Use Case Scenario #1

An automobile manufacturer and a paint supplier desire to coordinate and collaborate in the development, selection and implementation of one or more paint formulations. The paint supplier formulates a palette of colors and effects for review by the automobile manufacturer. In a preferred collaboration methodology, the color palette is developed using color formulation software provided by X-Rite, Inc., the assignee of the present application, and the manufacturer and supplier exchange physical samples and electronic data to facilitate the collaborative effort. Electronic data is advantageously facilitated with visual appearance management software/solutions, e.g., monitor optimizers and/or auto software.

Based on the manufacturer's selection(s), the supplier develops production recipes and processes using robotic spray booths. A series of panels are then sprayed to create a design of experiment (DOE) around formulation and process variations in order to establish baseline tolerances for full appearance. DNA prints are created for each panel and the expression values computed for each variant relative to the sample selected by the manufacturer. Recipe variants are tested based on variations of pigment grind, e.g., based on grind samples at 50% of the original, 75% of the original, and over grind.

These expression values are used to establish baseline tolerances for DNA distortion (e.g., formulation and lot to lot variation) and expression (e.g., process flow/atomization) magnitudes by interpolating the BRDF patterns between the original sample and the variants. Using the DNA results from the variant study, the minimum perceptual limit and acceptable perceptual production limits for all illumination/observation conditions are determined.

The formulation may then be released by the supplier for production and a final run of panels, e.g., 1000 panels. The panels are graded and sorted to create the QA masters for use at various manufacturing and supply-related locations, and for in-house supplier use. DNA prints are automatically computed for each plate and sorted by process around the desired DNA centroid. A virtual standard centroid and tolerances for each print group are also created for distribution with the master plates. Of note, the DNA prints represent all possible viewing conditions, i.e., total appearance, thereby ensuring accuracy.

Colorimetric values and DNA's are created from the collected measurements and used to compare to the samples provided to the manufacturer. Once the baseline recipe, process, and formulation are released for production, the process of transferring to others involved in the manufacturing process may commence. For example, the automobile manufacturer may receive the DNA files from the supplier and import them into a software system. The DNA database immediately provides a master fingerprint along with a 3D set of tolerances that would help guide the manufacturer and its QC team to implement production.

Exemplary Use Case Scenario #2

An automobile manufacturer has been engaged in production for a period of time, e.g., 3 months. A manufacturing location desires to ensure that the color appearance of its automobiles matches the master standard in all respects, e.g., regardless of lighting and/or viewing angle. DNA tolerances according to the present disclosure are used to monitor production. Standards and tolerances are established for production line(s) and, using a portable color measuring apparatus according to the present disclosure, manufacturing personnel are able to track the DNA process, formulation, and recipe expression tolerances, as well as the change in those tolerances (dF, dFb, dFg, dFr). Colorimetric measurement may only be necessary when the process drift indicator signals an out-of-tolerance condition. Because manufacturing personnel can directly relate the process tolerances to the nominal condition, process parameters may be adjusted based on the new tolerance statistics directly.

In the event a measurement indicates that the dF tolerances are out of range, the systems, apparatus and method of the present disclosure facilitate prompt and efficient troubleshooting and corrective action. For example, by comparing the measurement results to the process standard, manufacturing personnel may determine that a low atomization/low flow condition exists. In response, an adjustment to the flow and atomization settings may be made and confirmatory measurements taken. A series of iterations may be necessary to achieve an appropriate settings.

Because each paint system has a unique "DNA" represented by the points plotted in 3D space and that pattern is dependent on the recipe for the paint and the process settings used, corrective action is facilitated according to the present disclosure. The closer the two DNA's for two samples are, the closer they will appear under all viewing conditions. If something changes, the DNA would move in space and/or change shape. By determining how much the DNA's change over time (e.g., with tracking reports) and whether the change is in shape, position or both, it is possible to determine the cause of the problem. Indeed, exemplary instruments of the present disclosure can overlay and scale the measurements for analysis and corrective action. For example, it may become apparent—after scaling—that it was the same paint coating, and that therefore the production line issue must have been caused by a process change.

Exemplary Use Case Scenario #3

After a period of manufacture, it is noted that measurements indicate something has changed with respect to the body paint. Although the color looks correct, the measurements indicate the line is now running at the limit of the allowable tolerances. The issue is not yet visually perceivable but, if the process is allowed to continue to drift, the color issue will become visually apparent. Manufacturing personnel are confronted with a need to diagnose the problem, e.g., to determine if the issue may have been caused by the paint spray equipment, a new batch of paint, or some other issue. In troubleshooting the issue, measurements are taken of multiple body part locations, e.g., the fenders and the hood.

Once the data is collected, the manufacturing personnel advantageously view the DNA shapes and check the xA plots and xS plots. The xS plots look identical to the master standard, so they are confident the paint formulation has not changed. However, the xA may be a different size relative to the Master Panel data. On this basis, the manufacturing personnel may decide to compare the dF's for the hood and door panels to the Master sample data. If they look different, the Delta dF's may be plotted, which might show that the hood is in fact different as compared to the door, even though they are sprayed at the same time. This phenomenon may suggest that the particle size has changed, e.g., due to larger/heavier flakes falling out of the droplet cloud and not making it to the vertical sides of the automobile body. Of note, if only the process had varied, the Delta dF's for the hood and door panel would have been similar.

These types of issues may be caused by under-grinding or over-grinding of pigment, or an incorrect flake size, e.g., due to settling. Sampling of the incoming lot of flakes is not always representative of how an entire lot will behave. A panel study on the pigment may be helpful in diagnosing the problem, e.g., to determine if the process may have been impacted by changes in humidity and temperature. A panel study generally involves grinding the current lot of pigment to various levels from under grind to over grind. The panels can then be compared, inter alia, to the original master panel study. For example, the over ground results of the panel study may match up with the master panel study, suggesting that humidity is the issue. Corrective action may involve a shortening of the grinding cycle for the next lot of material.

According to the above-noted implementation of the disclosed system/method, corrective action is possible before the process is out of control and/or before someone notices a visual difference. Absent early corrective action, production vehicles would likely have been processed with a color variant beyond acceptable tolerances.

Exemplary Use Case Scenario #4

A bumper manufacturer (OEM) for an automobile manufacturer receives the master panels and associated DNA database for a new bumper from the manufacturer. A sample lot is provided for the OEM's use in manufacturing the bumpers.

To permit sourcing of the underlying paint from multiple sources (or from an alternative source relative to the developer of the relevant paint), a process study is completed to understand the paint formulation. Based on the measurement results, the OEM determines that a reasonable match can be achieved, but by comparing the DNA prints, the dF's, and the dDNA's, it is apparent that the current formulation and the new formulation are different, requiring the OEM to hold tighter process tolerances to allow for lot to lot variations in paint, while not resulting in a difference in appearance under certain lighting conditions.

Based on the results of the process study, the OEM uses the xA values to establish a virtual process centroid for the formulation. According to the present disclosure, the OEM is able to compare first master panel values to those from the process study and immediately identify the closest samples. Using the DNA results, the disclosed software/system estimates the "ideal" xA values for the DNA that would provide the best match to the master and the largest tolerances. The OEM may use the differences in process settings and their associated xA values to estimate the ideal process settings. Using baseline process settings, the OEM can prepare sprayed samples for measurement. Based on the reasonably close match in DNA and, after colorimetric confirmation checks, the OEM is able to move forward with OEM manufacture of the new bumper.

It is to be understood that the figures and descriptions of the present invention have been simplified to illustrate elements that are relevant for a clear understanding of the present invention, while eliminating, for purposes of clarity, other elements, such as, for example, some specific tasks of the non-execution service provider units described above, etc. Those of ordinary skill in the art will recognize that these and other elements may be desirable. However, because such elements are well known in the art and because they do not facilitate a better understanding of the present invention, a discussion of such elements is not provided herein.

As used herein, a "computer" or "computer system" may be, for example and without limitation, either alone or in combination, a personal computer (PC), server-based computer, main frame, server, microcomputer, minicomputer, laptop, personal data assistant (PDA), cellular phone, pager, processor, including wireless and/or wireline varieties thereof, and/or any other computerized device capable of configuration for processing data for standalone application and/or over a networked medium or media. Computers and computer systems disclosed herein may include operatively associated memory for storing certain software applications used in obtaining, processing, storing and/or communicating data. It can be appreciated that such memory can be internal, external, remote or local with respect to its operatively associated computer or computer system. Memory may also include any means for storing software or other instructions including, for example and without limitation, a hard disk, an optical disk, floppy disk, ROM (read only memory), RAM (random access memory), PROM (programmable ROM), EEPROM (extended erasable PROM), and/or other like computer-readable media.

The various modules 916, 918 of the system 901 may be implemented as software code to be executed by a processor(s) of the system 901 or any other computer system using any type of suitable computer instruction type. The software code may be stored as a series of instructions or commands on a computer readable medium. The term "computer-readable medium" as used herein may include, for example, magnetic and optical memory devices such as diskettes, compact discs of both read-only and writeable varieties, optical disk drives, and hard disk drives. A computer-readable medium may also include memory storage that can be physical, virtual, permanent, temporary, semi-permanent and/or semi-temporary. A computer-readable medium may further include one or more data signals transmitted on one or more carrier waves.

While several embodiments of the invention have been described, it should be apparent that various modifications, alterations and adaptations to those embodiments may occur to persons skilled in the art with the attainment of some or all of the advantages of the present invention. It is therefore intended to cover all such modifications, alterations and adaptations without departing from the scope and spirit of the present invention as defined by the appended claims.

We claim:

1. An apparatus for measuring spectral data of a surface, the apparatus comprising:
   one or more light sources for illuminating a surface;
   one or more sensors for receiving light reflected by the surface; and
   a computer in communication with the plurality of sensors;
   wherein the apparatus is adapted to receive light reflected by the surface in each of a plurality of reflectance directions; and
   wherein the computer is programmed to calculate a plurality of directional responses of the surface based on the received light in each of the plurality of reflectance directions, wherein each directional response is for a different wavelength or range of wavelengths, and wherein each directional response is calculated based on a vector sum of reflectance vectors over the plurality of reflectance directions at a corresponding wavelength or wavelength range.

2. The apparatus of claim 1, wherein reflectance direction is defined relative to a specular direction and an in-plane projection of an illumination direction orthogonal to the specular direction.

3. The apparatus of claim 1, wherein the received light is from at least a first, second and third reflectance directions, and wherein the first, second, and third reflectance directions are not coplanar.

4. The apparatus of claim 1, wherein the one or more light sources includes a first light source incident on the surface from a first illumination direction; and
   wherein the one or more sensors includes a plurality of sensors adapted to receive light originated from the first light source along the first illumination direction and reflected by the surface, wherein the plurality of sensors comprises:
   a first sensor adapted to receive light reflected by the surface in a first reflectance direction;
   a second sensor adapted to receive light reflected by the surface in a second reflectance direction; and
   a third sensor adapted to receive light reflected by the surface in a third reflectance direction.

5. The apparatus of claim 1, wherein each directional response is scaled based on a vector sum of an ideal white Lambertian reflector.

6. The apparatus of claim 1, wherein the computer is further programmed to generate a spectral representation defined by the directional endpoints of the plurality of directional responses.

7. The apparatus of claim 1, wherein the vector sum is a weighted vector sum.

8. The apparatus of claim 6, wherein the generated spectral representation is selected from the group consisting of a two-dimensional spectral representation and a three-dimensional representation and wherein a coordinate system for the generated spectral representation is defined by two or more axes selected from a group consisting of a z-axis corresponding to a specular direction, a y-axis corresponding to a projection of the illumination direction orthogonal to the specular direction, and an x-axis corresponding to a cross-product of the specular direction and a projection of the illumination direction orthogonal to the specular direction.

9. The apparatus of claim 6, further comprising a database for storing one or more spectral representations for known surfaces, wherein the computer is further programmed to compare the generated spectral representation to a reference spectral representation, wherein the reference spectral representation is one of (i) a stored spectral representations and (ii) a spectral representation derived therefrom.

10. The apparatus of claim 7, wherein weighting associated with the weighted vector sum is determined based on reflectance factors for each reflectance direction.

11. The apparatus of claim 7, wherein weighting associated with the weighted vector sum is used to reduce or exclude specular reflection.

12. A method for measuring spectral data of a surface, the method comprising:
receiving at one or more sensors light reflected by a surface in each of a plurality of reflectance directions,
calculating, using a computer, a plurality of directional responses of the surface based on the received light in each of the plurality of reflectance directions, wherein each directional response is for a different wavelength or range of wavelengths, and wherein each directional response is calculated based on a vector sum of reflectance vectors over the plurality of reflectance directions at a corresponding wavelength or wavelength range.

13. The method of claim 12, wherein reflectance direction is defined relative to a specular direction and an in-plane projection of an illumination direction orthogonal to the specular direction.

14. The method of claim 12, further comprising populating a database with one or more stored spectral representations of known surfaces.

15. The method of claim 12, further comprising generating a spectral representation defined by directional endpoints of the plurality of directional responses.

16. The method of claim 12, further comprising comparing the generated spectral representation or a derivative thereof relative to a reference spectral representation.

17. The method of claim 15, wherein the generated spectral representation is selected from the group consisting of a two-dimensional spectral representation and a three-dimensional representation and wherein a coordinate system for the generated spectral representation is defined by two or more axes selected a group consisting of a z-axis corresponding to a specular direction, a y-axis corresponding to a projection of the illumination direction orthogonal to the specular direction, and an x-axis corresponding to a cross-product of the specular direction and a projection of the illumination direction orthogonal to the specular direction.

18. The method of claim 15, wherein the generated spectral representation is used to represent, determine, assess or control at least one of (i) optical properties of the surface, (ii) formulation characteristics related to the surface and (iii) process factors related to the surface.

19. The method of claim 16, wherein the derivative of the generated spectral representation is a spectral representation derived by applying one or more transformation factors to the generated spectral representation.

20. The method of claim 16, wherein the comparing the generated spectral representation or a derivative thereof relative to the reference spectral representation includes calculating the square root of the sum of the squared distances between the reference spectral representation and the generated spectral representation or the derivation thereof.

21. The method of claim 16, wherein the comparing the generated spectral representation or a derivative thereof relative to the reference spectral representation includes determining colorimetric data for the generated spectral representation or for a derivation thereof.

22. The method of claim 16, further comprising determining one or more transformation factors for the generated spectral representation or for the derivative thereof, the one or more transformation factors including at least one of (i) a translation factor, (ii) a rotation factor, (iii) an alignment factor and (iv) a scale factor.

23. The method of claim 20, further comprising applying a non-linear scale before calculating the square root of the sum of the squared distances.

24. The method of claim 21, wherein the colorimetric data includes a set of vectors determined based on standard XYZ data in each of a y-z plane, an x-z plane and an x-y plane based on a coordinate system defined by a z-axis corresponding to a specular direction, a y-axis corresponding to a projection of the illumination direction orthogonal to the specular direction and an x-axis corresponding to a cross-product of the specular direction and a projection of the illumination direction orthogonal to the specular direction.

25. The method of claim 24, further comprising determining at least one of (i) L, a, b data and (ii) color difference data based on magnitudes of the vectors in the set of vectors.

26. The method of claim 22, wherein the comparing the generated spectral representation relative to the reference spectral representation or the derivative thereof includes comparing the one or more determined transformation factors relative to one or more transformation factors for the reference spectral representation.

27. The method of claim 22, wherein the one or more transformation factors includes a translation factor determined with respect to an average directional response, wherein the translation factor is determined relative to an origin point based on a coordinate system defined by a z-axis corresponding to a specular direction, a y-axis corresponding to a projection of the illumination direction orthogonal to the specular direction and an x-axis corresponding to a cross-product of the specular direction and a projection of the illumination direction orthogonal to the specular direction.

28. The method of claim 22, wherein the one or more transformation factors includes a rotation factor determined based on a rotation of a best fit plane relative to a y-z plane based on a coordinate system defined by a z-axis corresponding to a specular direction, a y-axis corresponding to a projection of the illumination direction orthogonal to the specular direction and an x-axis corresponding to a cross-product of the specular direction and a projection of the illumination direction orthogonal to the specular direction.

29. The method of claim 22, wherein the one or more transformation factors includes an azimuth rotation factor determined based on a rotation in an x-y plane and a colatitude rotation factor determined based on a rotation in an x-z plane.

30. The method of claim 22, wherein the one or more transformation factors includes an alignment factor determined based on a rotation of the generated spectral representation or the derivation thereof in a y-z plane based on a coordinate system defined by a z-axis corresponding to a specular direction, a y-axis corresponding to a projection of the illumination direction orthogonal to the specular direction and an x-axis corresponding to a cross-product of the specular direction and a projection of the illumination direction orthogonal to the specular direction.

31. The method of claim 22, wherein the one or more transformation factors includes a scale factor and an alignment factor determined simultaneously using a least squares fit to minimize the distance between a standard spectral representation and the generated spectral representation or the derivation thereof.

32. The method of claim 31, wherein the one or more transformation factors includes a scale factor, wherein the scale factor is used to determine whether differences between the generated spectral representation and the reference spectral representation are on account of process differences or on account of formulation differences.

* * * * *